US006930095B2

(12) United States Patent
Bichko

(10) Patent No.: US 6,930,095 B2
(45) Date of Patent: Aug. 16, 2005

(54) HEPATITIS C VIRUS CONSTRUCTS CHARACTERIZED BY HIGH EFFICIENCY REPLICATION

(75) Inventor: Vadim Bichko, Waltham, MA (US)

(73) Assignee: Anadys Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 10/005,469

(22) Filed: Nov. 7, 2001

(65) Prior Publication Data

US 2002/0155133 A1 Oct. 24, 2002

Related U.S. Application Data

(60) Provisional application No. 60/245,866, filed on Nov. 7, 2000.

(51) Int. Cl.[7] ............... A61K 31/7115; A61K 31/713; A61K 39/29; C12N 5/00; C12N 5/08; C12N 5/10; C12N 5/22; C12N 7/01; C12N 7/08; C12N 15/85; C12N 15/87; C12N 15/90; C07H 21/00

(52) U.S. Cl. ............... 514/44; 436/23.1; 436/23.4; 436/23.72; 436/24.1; 435/320.1; 435/325; 435/235.1; 435/236; 424/186.1; 424/189.1

(58) Field of Search ............... 536/23.1, 53.4, 536/23.72, 24.1, 23.7; 435/235.1, 236, 230.1, 370; 424/186.1, 189.1, 228.1, 202.1, 204.1, 262.1

(56) References Cited

U.S. PATENT DOCUMENTS

| 5,679,342 A | 10/1997 | Houghton et al. ........ 424/93.21 |
| 5,874,565 A | 2/1999 | Rice et al. ................. 536/24.1 |
| 6,127,116 A | 10/2000 | Rice et al. |
| 6,392,028 B1 | 5/2002 | Rice, III et al. |
| 6,630,343 B1 | 10/2003 | Bartenschlager |
| 6,706,874 B2 | 3/2004 | Kukolj et al. |

FOREIGN PATENT DOCUMENTS

| CA | 2303526 | 10/2000 | |
| WO | WO 98/39031 | 9/1998 | .......... A61K/39/29 |

OTHER PUBLICATIONS

Sequence search report.*
Blight et al., Science, 2000;290:1972–1974.
Marshall, Eliot, Science, 2000;290:1870–1871.
Lohmann et al., J. Virology, 2001;75(3):1437–1449.
Bartenschlager, J. Viral Hepatitis, 1999, 6:165–181.
Bartenschlager and Lohmann, J. Gen. Virol., 2000, 81:1631–1648.
Baumert et al. J. Virol., 1998, 72(5):3827–3836.
Baumert et al., Gastroenterology, 1999, 117:1397–1407.
Beard et al., Hepatology, 1999, 30:316–324.
Behrens et al., J. Virol., 1998, 72:2364–2372.
Blight and Gowans, Viral Hepatitis Rev., 1995, 1:143–155.
Bouffard et al., J. Infect. Diseases, 1992, 166:1276–1280.
Boyer et al., Virology, 1994; 198:415–426.
Bukh et al., Seminars in Liver Disease, 1995; 15(1):41–63.
Bukh et al., Clin. and Exp. Rheumatol., 1995; 13(Suppl. 13):S3–S7.
Darai et al., J. Infect. Dis., 1978, 137:221–226.
Dash et al., Am. J. Pathol., 1997, 151(2):363–373.
Fournier et al., J. Gen. Virol., 1998, 79:2367–2374.
Iacovacci et al., Res. Virol., 1993, 144:275–279.
Ikeda et al., Virus Res., 1998, 56:157–167.
Ilan et al., Hepatology, 1999, 29:553–562.
Kato et al., Jpn. J. Cancer Res., 1996, 87:787–792.
Khromykh and Westaway, J. Virol., 1997, 71:1497–1505.
Kohara M., J. Dermatol. Sci., 2000, 22:161–168.
Kolykhalov et al., J. Virol., 1996, 70(6):3363–3371.
Kolykhalov et al., Science, 1997, 277:570–574.
Kolykhalov et al., J. Virol., 2000, 74(4):2046–2051.
Lanford et al., 1994, Virology, 202:606–614.
Lieber et al., Journal of Virology, 1996; 70(12):8782–8791.
Liljeström and Garoff, Biotechnol., 1991, 9:1356–1361.
Lohmann et al. Science, 1999, 285:110–113.
Mizutani et al., J. Virol., 1996, 70:7219–7223.
Moormann et al., J. Virol., 1996; 70(2):763–770.
Moradpour et al., Biochem. Biophys. Res. Comm., 1998, 246:920–924.
Müller et al., J. Gen. Virol., 1993, 74:669–676.
Nakabayashi et al., Cancer Res., 1982; 42:3858–3863.
Nakajima et al., J. Virol., 1996, 70(5):3325–3329.
Petersen et al., Proc. Natl. Acad. Sci. USA, 1998, 95:310–315.
Pileri et al., Science, 1998; 282:938–941.
Rosen and Gretch, Mol. Medicine Today, 1999, 5: 393–399.
Ruiz et al., J. Viral Hepatitis, 1999; 6:17–34.
Rumin et al., J. Gen. Virol., 1999, 80:3007–3018.
Shimizu et al., Proc. Natl. Acad. Sci. USA, 1992, 89:5477–5481.
Shimizu and Yoshikura, J. Virol., 1994, 68(12):8406–8408.
Seipp et al., J. Gen. Virol., 1997; 78:2467–2476.
Sugiyama et al., J. Gen. Virol., 1997, 78:329–336.
Tanaka et al., Biochem. Biophys. Res. Comm., 1995, 215(2):744–749.
Tanaka et al., J. Virol., 1996, 70(5):3307–3312.
Walter et al., Hepatology, 1996, 24:1–5.
Xie et al., Virology, 1998, 244:513–520.
Yamada et al.,Virology, 1996, 223:255–261.
Yan et al., J.Cancer Res. Clin. Oncol., 1996, 122:283–288.
Yan et al., J.Cancer Res. Clin. Oncol., 1996, 122:289–295.
Yanagi et al., Proc. Natl. Acad. Sci. USA, 1997, 94:8738–8743.
Yanagi et al., Virology, 1998, 244:161–172.
Yanagi et al., Proc. Natl. Acad. Sci. USA, 1999; 96:2291–2295.
Yoo et al. J. Virol., 1995, 69:32–38.
Zignego et al., J. Hepatol., 1992, 15:382–386.

* cited by examiner

Primary Examiner—James Housel
Assistant Examiner—Bao Qun Li
(74) Attorney, Agent, or Firm—Darby & Darby

(57) ABSTRACT

The present invention relates to recombinant hepatitis C virus (HCV)-derived nucleic acids and to stable rapidly growing cell clones derived from human hepatoma Huh-7 cell line and supporting high titer replication of said recombinant HCV nucleic acids. The subgenomic HCV replicons and cell clones of the instant invention represent the in vitro system of choice for studies of HCV propagation, anti-viral drug screening, and vaccine development.

8 Claims, 4 Drawing Sheets

HEPATITIS C VIRUS CONSTRUCTS CHARACTERIZED BY HIGH EFFICIENCY REPLICATION

This application claims the benefit of U.S. Provisional Application No. 60/245,866 filed Nov. 7, 2000, which is hereby incorporated by reference in its entirety.

FIELD OF THE INVENTION

The present invention relates to recombinant hepatitis C virus (HCV)-derived nucleic acids and to stable rapidly growing cell clones supporting their efficient replication.

BACKGROUND OF THE INVENTION

Infection by hepatitis C virus (HCV) is a compelling human medical problem. HCV is recognized as the causative agent for most cases of non-A and non-B hepatitis, with an estimated worldwide prevalence of 170 million cases (i.e., 2–3%) (Choo et al., Science, 1989, 244:359–362; Kuo et al., Science, 1989, 244:362–364; Purcell, FEMS Microbiol. Rev., 1994, 14:181–192; Van der Poel, In: *Current Studies in Hematology and Blood Transfusion*, Reesink ed., Basel: Karger, pp. 137–163, 1994). Four million individuals may be infected in the United States alone (Alter and Mast, Gastroenterol. Clin. North Am., 1994, 23:437–455).

HCV is primarily transmitted parenterally, although sexual and perinatal transmission do appear to occur. At present, no risk factor has been identified in about 40% of HCV-infected individuals in the US (Alter, Infect. Agents Dis., 1993, 2:155–166). Upon first exposure to HCV, only about 10% or less of infected individuals develop acute clinical hepatitis, while others appear to resolve the infection spontaneously. In most instances, however, the virus establishes a chronic infection that persists for decades, leading in about 50% of all cases to chronic hepatitis, which can, in turn, develop into liver cirrhosis and/or hepatocellular carcinoma (Iwarson, FEMS Microbiol. Rev., 1994, 14:201–204; Kew, ibid. pp.211–220; Saito et al., Proc. Natl. Acad. Sci. USA, 1990, 87:6547–6549).

Apart from liver cells, HCV can also replicate in peripheral blood mononuclear cells (PBMCs) both in vivo and in experimentally infected B- and T-cell lines (U.S. Pat. Nos.: 5,679,342 and 5,968,775). Such a lymphotropism may account for the numerous immunological disorders, in particular type II and type III cryoglobulinaemia, observed in more than 50% of chronic hepatitis C patients (Esteban et al., In: *Hepatitis C Virus*, Reesink ed., Basel: Karge, 1998, pp. 102–118).

HCV Structure and Genome Organization

Given the high prevalence of the virus, HCV has become a focus of intensive research (for recent review see Bartenschlager and Lohmann, J. Gen. Virol., 2000, 81:1631–1648; Rosen and Gretch, Mol. Medicine Today, 1999, 5: 393–399). Originally cloned in 1989 (Choo et al., supra), the viral genome is now well characterized. HCV is a (+) strand enveloped RNA virus, i.e. its genome is represented by a coding single stranded RNA (cRNA) which is packaged with the structural proteins in a viral particle surrounded by a host cell-derived membrane. HCV has been classified as the sole member of a distinct genus called hepacivirus in the family *Flaviviridae*, which includes, e.g., the flaviviruses and the animal pathogenic pestiviruses. Its genome has a length of approximately 9.6 kb and its single, long open reading frame (ORF) encodes an approximately 3000-amino acid polyprotein that is proteolytically cleaved into a set of distinct products (FIG. 1 [prior art]; see also Rice, In: *Virology*, Fields et al. eds., Lippincott-Raven, 1996, Vol.1, pp.931–960; Clarke, J. Gen. Virol., 1997, 78:2397).

The HCV ORF is flanked at the 5' and 3' ends by nontranslated regions (NTRs). Translation of the ORF is directed via an approximately 340 nucleotide (nt) long 5' NTR functioning as an internal ribosome entry site (IRES) and permitting the direct binding of ribosomes in close proximity to the start codon of the ORF (Tsukiyama-Kohara et al., J. Virol., 1992, 66:1476–1483; Wang et al., J. Virol., 1993, 67:3338–3344). The first approximately 40 nucleotides of the 5' NTR are not required for translation but, based on analogy with other (+) strand RNA viruses, are involved most likely in RNA replication (Boyer and Haenni, Virology, 1994, 198:415–426). The 3' NTR has a tripartite structure composed of a variable sequence following the stop codon of the ORF, a poly(U) tract of heterogeneous length and a highly conserved 98 nucleotide sequence essential for replication in vivo (Kolykhalov et al., J. Virol., 1996, 70:3363; Tanaka et al., Biochem. Biophys. Res. Comm., 1995, 215:744; Tanaka et al., J. Virol., 1996, 70:3307; Yamada et al., Virology, 1996, 223:255; Yanagi et al., Proc. Natl. Acad. Sci. U.S.A., 1999, 96:2291; Kolykhalov et al., J. Virol., 2000, 74:2046–2051).

The HCV polyprotein is cleaved co- and post-translationally by cellular and viral proteinases into ten different products, with the structural proteins located in the N-terminal one-third and the non-structural (NS) proteins (i.e., proteins which are not expected to be constituents of the virus particle) in the remainder (FIG. 1; reviewed in Bartenschlager and Lohmann, supra; Bartenschlager, J. Viral Hepatitis, 1999, 6:165–181; Reed and Rice, In: *Hepatitis C Virus*, Reesink ed., Basel: Karger, 1998, pp. 1–37). The first cleavage product of the polyprotein is a highly basic core protein, which is the major constituent of the nucleocapsid (Yasui et al., J. Virol., 1998, 72:6048–605) and is involved in modulation of several cellular processes leading to induction of hepatocellular carcinoma (Chang et al., J. Virol., 1998, 72: 3060–3065; Chen et al., J. Virol., 1997, 71:9417–9426; Matsumoto et al., ibid., pp.1301–1309; Moriya et al., Nature Med.,1998, 4:1065–1067). Envelope proteins E1 and E2 are highly glycosylated type 1 transmembrane proteins, forming two types of stable heterodimeric complexes (Deleersnyder et al., J. Virol., 1997, 71:697–704). In addition, E2 was shown to interact with the interferon (IFN)-induced double-stranded RNA-activated protein kinase PKR, allowing continuation of translation of HCV RNA in the presence of IFN (Taylor et al., Science, 1999, 285:107–110). Protein p7, located at the C-terminus of E2, is a highly hydrophobic polypeptide of unknown function. Most of the nonstructural proteins NS2-5B are required for replication of the viral RNA (Lohmann et al., Science, 1999, 285:110–113). NS2 and the N-terminal domain of NS3 constitute the NS2-3 proteinase, catalysing cleavage at the NS2/3 site (Grakoui et al., 1993, Proc. Natl. Acad. Sci. USA, 1993, 90:10583–10587; Hijikata et al., J. Virol., 1993, 67:4665–4675; Hirowatari et al., Arch. Virol., 1993, 133:349–356). NS3 is a bifunctional molecule carrying, in the N-terminal approximately 180 residues, a serine-type proteinase responsible for cleavage at the NS3/4A, NS4A/B, NS4B/5A and NS5A/B sites and, in the C-terminal remainder, NTPase/helicase activities essential for translation and replication of the HCV genome (Bartenschlager et al., J. Virol., 1993, 67:3835–3844; Eckart et al., Biochem. Biophys. Res. Comm., 1993, 192:399–406; Grakoui et al., J. Virol., 1993, 67:2832–2843; Gwack et al., Biochem. Biophys. Res. Comm., 1996, 225:654–659; Hong et al., J. Virol., 1996, 70:4261–4268; Kim et al., Biochem. Biophys. Res. Comm., 1995, 215:160–166; Suzich et al., J. Virol., 1993, 67:6152–6158; Tai et al., J. Virol., 1996, 70:8477–8484; Tomei et al., J. Gen. Virol., 1993, 77:1065–1070; Kolykhalov et al., 2000, supra). In addition, NS3 may interfere with host cell functions by inhibiting protein kinase A (PKA)-mediated signal transduction and/or by inducing cell transformation (Borowski et al., Eur. J. Biochem., 1996, 237:611–618; Sakamuro et al., J. Virol., 1995, 69:3893–3896). NS4A is an essential cofactor of the NS3 proteinase and is required for efficient polyprotein processing (Bartenschlager et al., J. Virol., 1994, 68:5045–5055; Failla et al., ibid., pp. 3753–3760; Lin et al., ibid., pp. 8147–8157; Tanji et al., J. Virol., 1995, 69:1575–1581). The function of the hydrophobic NS4B is so far unknown. NS5A is a highly phosphorylated protein (Asabe et al., J. Virol., 1997, 71:790–796; Kaneko et al., Biochem. Biophys. Res. Comm., 1994, 205:320–326; Koch and Bartenschlager, J. Virol., 1999, 73:7138–7146; Neddermann et al., ibid., pp. 9984–9991; Tanji et al., J. Virol., 1995, 69:3980–3986) which appears to interfere with the antiviral effect of IFN by binding to PKR (Gale et al., Virology, 1997, 230:217–227; Gale et al., Mol. Cell Biol., 1998, 18:5208–5218) and may also play role in RNA replication. NS5B was identified as the RNA-dependent RNA polymerase (RdRp) (Al et al., Virus Res., 1998, 53:141–149; Behrens et al., EMBO J., 1996, 15:12–22; Lohmann et al., J. Virol., 1997, 71:8416–8428; Yamashita et al., J. Biol. Chem., 1998, 273:15479–15486; Yuan et al., Biochem. Biophys. Res. Comm., 1997, 232:231–235).

HCV Replication and Variability

Similarly to related positive (+) strand RNA viruses, HCV replication occurs by means of a negative (−) strand RNA intermediate and is catalyzed by the NS proteins forming a cytoplasmic membrane-associated replicase complex. HCV replication cycle can be summarized as follows (FIG. 2 [prior art]): (1) penetration of the host cell and liberation of the genomic RNA (cRNA) from the virus particle into the cytoplasm; (2) translation of the input cRNA, processing of the polyprotein and formation of a replicase complex associated with intracellular membranes; (3) utilization of the input (+) strand for synthesis of a (−) strand RNA intermediate; (4) production of new (+) strand RNA molecules which can be used for synthesis of new (−) strands, for polyprotein expression or for packaging into progeny virions; (5) release of virus from the infected cell via cellular secretion pathway resulting in formation of cell-derived viral membrane envelope.

The dynamics of HCV replication can be deduced from the rapid rates of virus production and emergence of mutants. Analysis of viral dynamics during antiviral treatment of patients with IFN-α revealed a virion half-life of 3–5 hours and a clearance and production rate of approximately $10^{12}$ particles per day (Zeuzem et al., Hepatology, 1998, 28:245–252; Neumann et al., Science, 1998, 282:103–107; Ramratnam et al., Lancet, 1999, 354:1782–1785). Although in absolute amounts these numbers are high, they are not with respect to a single cell, corresponding to a virion production rate of 50 particles per hepatocyte per day (Neumann et al., supra).

Another feature of HCV replication is a rapid generation of virus variants. Early studies of the mutation rate of HCV in chronically infected humans and chimpanzees demonstrated that this virus mutated very rapidly with the rate of change varying between different genomic regions (Ogata et al., Proc. Natl. Acad. Sci. USA, 1991, 88:3392–3396; Okamoto et al., Virology, 1992, 190:894–899). Thus, the highest mutation rate was found in the E1 and E2 genes with especially high rate observed in a short sequence encoding the domain located at the N-terminus of E2 protein (hence termed "hypervariable region 1" or "HVR1"). Accordingly, even within a single patient HCV does not exist as a single entity but rather as a collection of microvariants of a predominant "master sequence", a phenomenon that has been referred to as quasispecies (reviewed in Bukh et al., Semin. Liv. Dis., 1995, 15:41–63; Bukh et al., Clin. Exp. Rheumatol., 1995, 13(suppl.):S3-S7; Holland et al., Curr. Topics Microbiol. Immunol., 176:1–20). The master sequence, as well as the consensus sequence of the quasispecies sequence population have been found to change sequentially during the infection. The production of such large number of variants is primarily due to the high error rate of the viral RdRp that, based on analogies with RdRps of other (+) strand RNA viruses, is expected to be in the range of $10^4$. Using comparative sequence analyses of HCV genomes isolated over intervals of 8 or 13 years, a mutation rate of $1.44 \times 10^{-3}$ or $1.92 \times 10^{-3}$ base substitutions per site per year was found, respectively (Ogata et al., supra; Okamoto et al., supra). The high variation observed with HCV replication may also account for the fact that a significant fraction of virus genomes appear to be defective (Martell et al., J. Virol., 1992, 66:3225–3229).

The biological consequences of quasispecies include: (i) the development of escape mutants to humoral and cellular immunity leading to the establishment of a persistent infection; (ii) variable cell tropism (e.g., lymphotropic vs hepatotropic); (iii) vaccine failure, and (iv) rapid development of drug resistance (Bukh et al., Semin. Liv. Dis., supra). For example, it has been found that the HVR1 contains epitopes that elicit a specific humoral immune response and that sequential changes of HVR1 during infection resulted in the emergence of epitopes that were not recognized by pre-existing antibodies (Weiner et al., Proc. Natl. Acad. Sci. USA, 1992, 89:3468–72; Taniguchi et al., Virology, 1993, 195:297–301; Kato et al., J. Virol., 1993, 67:3923–30; Kato et al., J. Virol., 1994, 68:4776–84).

It is now well established that HCV exists as distinct genotypes among different HCV isolates with prevalence of each of the genotypes in specific geographical locations. Based on the genomic variability in the most highly conserved NS5B and E1 sequences, HCV has been classified into at least 9 major genetic groups (genotypes 1a, 1b, 1c, 2a, 2b, 3a, 7, 8, 9) with total over 30 subtypes (Bukh et al., Clin. Exp. Rheumatol., supra; Simmonds et al., J. Gen. Virol., 1993, 74:2391–2399). Several recent studies indicate that the extensive genetic heterogeneity of HCV may have important clinical implications, with genotype 1b (prevalent in the US and Europe) being associated with a more severe liver disease and a poorer response to interferon therapy (reviewed in Bukh et al., supra).

Anti-HCV Therapies

Despite the intense research, the only anti-HCV therapy currently available is administration of a high dose of IFN-α or a combination treatment with IFN-α and the nucleoside analogue ribavirin. However, only about 40% of all patients benefit from this treatment and develop a sustained response, demonstrating the urgent need for more effective antiviral therapeutics (Marcellin et al., Ann. Intern. Med., 1997, 127:875–881; Reichard et al., Lancet, 1998, 351:83–87).

As mentioned above, anti-HCV vaccine development has been hampered by the high degree of viral variability leading to efficient immune evasion and the lack of protection against reinfection, even with the same inoculum (Farci et al., Science, 1992, 258:135–140; Kao et al., J. Med. Virol., 1996, 50:303–308; Shimizu et al., 1994, J. Virol., 68:1494–1500; Wyatt et al., J. Virol., 1998, 72:1725–1730). Among the most promising approaches to vaccine development, is immunization with highly conserved HCV core protein alone or in combination with E1 and/or E2 envelope proteins, and/or NS3 protein (Major et al., 1995, J. Virol., 69:5798–5805; Tokushige et al., Hepatology, 1996, 24:14–20; Geissler et al., J. Immunol., 1997, 158:1231–1237; Inchauspe et al., Vaccine, 1997, 15:853–856).

In view of the reasonable scepticism over the "universal" anti-HCV vaccine, the importance of alternative therapies increases. Such therapies include without limitation: (i) small molecule inhibitors directed against specific viral targets (e.g., E1/E2 envelope proteins or NS3 protease/helicase); (ii) antisense oligonucleotides and ribozymes for the inhibition of HCV replication, and (iii) transdominant-negative proteins (Kim et al., Cell, 1996, 87:343–355; Love et al., ibid., 331–342; Yao et al., Nat. Struct. Biol., 1997, 4:463–467; Yan et al., Protein Sci., 1998, 7:837–847; Von Wizsaker et al., Hepatology, 1997, 26:251–255; Lieber et al., J. Virol., 1996, 70:8782–8791; Rosen and Gretch, supra; Saito et al., Gastroenterology, 1997, 112:1321–1330; Nakano et al., J. Virol., 1997, 71:7101–7109; Fournillier et al., Hepatology, 1998, 28:237–244; Wakita et al., J. Biol. Chem., 1994, 269:14205–14210; Mizutani et al., Biochem. Biophys. Res. Comm., 1995, 212:906–911; Alt et al., Hepatology, 1995, 22:707–717; Havecak et al., J. Virol., 1996, 70:5203–5212; Lima et al., J. Biol. Chem., 1997, 272:626–638; Alt et al., Arch. Virol., 1997, 142:589–599; Wu and Wu, Gastroenterology, 1998, 114:1304–1312; Sakamoto et al., J. Clin. Invest., 1996, 98:2720–2728; Ruiz et al., J. Viral Hepatitis, 1999, 6:17–34).

In Vivo and In Vitro Systems for HCV Infection

As the currently available chimpanzee models are too expensive to be practical for early stage evaluation of anti-HCV therapeutics, there is a need in the art to develop more manageable and efficient in vivo and in vitro model systems for HCV infection.

In an attempt to establish a small animal model Xie et al. (Virology, 1998, 244:513–520) experimentally inoculated *Tupaias* (*T. belangeri chinensis*), a tree shrew species which adapt and breed in the laboratory environment, are closely related to primates, and were previously shown to be susceptible to infection with the human rotavirus (Wan et al., Natl. Med. J. Chin., 1982, 62:461–465), herpes simplex virus type 1 and 2 (Darai et al., J. Infect. Dis., 1978, 137:221–226), and human hepatitis viruses A, B (both in vitro and in vivo), and Delta (Li et al., Chung. Hua. I. Hsueh. Tsa. Chih., 1995, 75:611–613; Walter et al., Hepatology, 1996, 24:1–5; Yan et al., J.Cancer Res. Clin. Oncol., 1996, 122:283–288 and 289–295; Zan et al., Acta Acad. Med. Sin., 1981, 3:148–152). Although, upon inoculation, only about one-quarter of the animals became infected with HCV and developed either transient or intermittent viraemia with rather low titers, the Tupaia animal model appears to be very promising. Recently, two potential alternatives have been described for the propagation of hepatitis B viruses that might be used for HCV as well. Both systems are based on the engraftment of human liver tissue into immuno-compromised mice (Ilan et al., Hepatology, 1999, 29:553–562; Petersen et al., Proc. Natl. Acad. Sci. USA, 1998, 95:310–315).

Although development of a small animal model is critical for studies of HCV pathophysiology and for assaying toxicology and pharmacokinetics of anti-HCV therapeutics, it is of primary importance to create a convenient and reliable cell culture-based assay system that supports HCV infection and replication and allows detailed molecular studies of HCV propagation and efficient high-throughput evaluation of anti-HCV therapeutics.

Until recently, in vitro research on HCV has depended largely on (i) analogies to the closely related flavi- and pestiviruses, (ii) characterization of recombinantly produced HCV proteins, (iii) infection of primary cell cultures with HCV-containing sera of infected individuals, and (iv) cultivation of primary cells derived from chronically infected tissues (Lanford et al., 1994, Virology, 202:606; Shimizu et al., Proc. Natl. Acad. Sci. U.S.A., 1992, 89:5477; Mizutani et al., J. Virol., 1996, 70:7219–7223; Ikeda et al., Virus Res., 1998, 56:157; Fournier et al., J. Gen. Virol., 1998, 79:2376). For example, HCV replication was reported in primary hepatocytes from humans or chimpanzees following infection with high titer HCV-containing serum (Fournier et al., supra; Iacovacci et al., Res. Virol., 1993, 144:275–279; Lanford et al., supra; Rumin et al., J. Gen. Virol., 1999, 80:3007–3018) and in PBMCs isolated from chronically infected patients (Bouffard et al., J. Infect. Diseases, 1992, 166:1276–1280; Müller et al., J. Gen. Virol., 1993, 74:669–676; Zignego et al., J. Hepatol., 1992, 15:382–386).

In the primary cell cultures HCV replication was detected using a number of highly sensitive methods: (i) detection of (−) strand replicative RNA intermediates by strand-specific reverse transcriptase-polymerase chain reaction (RT-PCR) or Nothern blot; (ii) determination of an increase of (+) strand RNA during the cultivation period using either b-DNA assay or quantitative RT-PCR; (iii) detection of inhibition of replication upon incubation of the cells with IFN-α or antisense oligonucleotides; (iv) the ability of the cell culture medium (containing viral particles) to cause infection upon addition to naive cells; (v) sequence analysis of HCV genomes or genome fragments to demonstrate genomic variability and selection of variants upon infection and cultivation, and (vi) detection of viral antigens in situ or upon isolation using, e.g., immunofluorescence, Western blotting, or flow cytometry.

It should be noted, however, that primary cell cultures are not routinely available, are hard to maintain, and suffer from poor reproducibility and a low level of HCV replication that can be measured only with highly sensitive techniques. Accordingly, numerous attempts have been made to develop stable HCV-replicating cell lines. Initially, these cell lines were also developed by infecting them with the virus isolated from infected individuals. Such HCV-infected cell lines, secondary monkey kidney cells CV-1 and human diploid fibroblasts VERO, are disclosed, for example, in the PCT Application No. WO 96/24662. With respect to hepatoma cell lines, the most detailed results are available for the non-neoplastic cell line PH5CH (Ikeda et al., 1998, supra; Kato et al., Jap. J. Cancer Res., 1996, 87:787–792). However, a strong selection for HCV variants in the HVR1 of the E2 protein was observed in this cell line suggesting that only certain variants can bind to or replicate in these cells. A similar decrease of complexity of viral quasispecies has been described for HCV propagated in primary human hepatocytes for up to 3 months (Rumin et al., supra).

HCV replication upon infection was also demonstrated in cultured cells derived from the T-cell lines MT-2, HPBMa10-2, and MOLT-4 and from the B-cell line Daudi. For example, in HPBMa10-2 and Daudi cells, long-term propagation of HCV for more than 1 year has been described (Nakajima et al., J. Virol., 1996, 70:3325–3329), and virus could be transmitted several times to naive cells by cocultivation (Shimizu and Yoshikura, J. Virol., 1994, 68:8406–8408). HCV-replicating B- and T-cell lines are also disclosed in the U.S. Pat. No. 5,679,342. However, similarly to PH5CH cells, it was found that only certain virus variants replicate in HPBMa10-2 and Daudi cells as well as in MT-2C cells, suggesting the selection of lymphotropic HCV quasispecies (Mizutani et al., J. Virol., 1996, supra; Sugiyama et al., J. Gen. Virol., 1997, 78:329–336).

Attempts to Create Stable Cell Lines Containing Self-Propagating Recombinant HCV Replicons The recent construction of cloned HCV genomes and demonstration of their ability to replicate and cause disease development after intrahepatic inoculation of chimpanzees (Beard et al., Hepatology, 1999, 30:316–324; Kolykhalov et al., Science, 1997, 277:570–574; Yanagi et al., Proc. Natl. Acad. Sci. USA, 1997, 94:8738; Yanagi et al., Virology, 1998, 244:161) has opened some new avenues to study HCV replication and pathogenesis. Specifically, it made feasible the development of stable cell cultures containing selectable HCV replicons. Compared to the infection of cell lines with HCV-containing patient material, the introduction of cloned virus genomes is superior because the inoculum is well defined and can be generated in high quantities. Most importantly, the genome can be manipulated at will, permitting a detailed genetic analysis of viral functions leading to successful development of anti-viral therapeutics.

Similarly to experience with several (+) strand RNA viruses (Boyer and Haenni, supra), it became clear with the first attempts to create self-replicating subgenomic HCV clones in culture that the use of in vitro synthesized RNA transcripts (cRNA) of defined structure (produced, e.g., using T7 or SP6 in vitro transcription system) is advantageous to transfection of DNA constructs. Indeed, direct transfection of cRNA avoids the involvement of the cell nucleus and therefore potential problems associated with transcriptional regulation, splicing, incorrect 5' and 3'-end processing, and nucleo-cytoplasmic transport (Dash et al., Am J. Pathol., 1997, 151:363–373).

However, in contrast to many other (+) strand RNA viruses, construction of self-replicating subgenomic HCV clones in culture turned out to be very difficult. Until recently, only a few successful attempts were reported, each lacking important controls and/or being somewhat controversial. Thus, Baumert et al. (J. Virol., 1998, 72:3827–3836) described assembly of poorly characterized HCV-like particles in insect cells upon introduction of a recombinant baculovirus containing the cDNA encoding HCV ORF. Dash et al. (supra) and Yoo et al. (J. Virol., 1995, 69:32–38) reported successful replication of putative HCV cRNA upon transfection in the human hepatoma cell lines Huh-7 and HepG2, respectively. However, both studies appear to be highly questionable as they describe the propagation of truncated HCV genomes lacking the authentic 3' NTR, which is essential for replication in vivo (Yanagi et al., 1999, supra; Kolykhalov et al., 2000, supra).

The most convincing evidence of a functional in vitro cell-based system for replication of recombinant HCV came from a recent report by Lohmann et al. (Science, 1999, 285:110–113). These authors have described selectable subgenomic HCV RNA molecules replicating after transfection into the human hepatoma cell line Huh-7. Similar subgenomic HCV replicons capable of propagating in tissue culture are disclosed in PCT Application No. WO 98/39031. Based on the assumption that high expression levels of the structural proteins might be cytotoxic (Moradpour et al., Biochem. Biophys. Res. Comm., 1998, 246:920–924) and the observation that for several (+) strand RNA viruses (e.g., alpha-, flavi- and pestiviruses) the structural proteins are not required for RNA replication (Behrens et al., J. Virol., 1998, 72:2364–2372; Khromykh and Westaway, J. Virol., 1997, 71:1497–1505; Liljestrom and Garoff, Biotechnol., 1991, 9:1356–1361), Lohmann et al. deleted the sequences of the structural proteins in their HCV-derived constructs. In addition, to allow selection for only those cells which support efficient HCV replication, the gene encoding the neomycin phosphotransferase (neo) and conferring resistance to the antibiotic G418, was introduced downstream of the HCV IRES (FIG. 3). A second IRES element was included to allow translation of the HCV NS proteins. Upon transfection of these bicistronic RNAs and selection in the presence of G418, only cells supporting replication of HCV-derived RNAs amplified the neo gene and developed resistance, whereas non-transfected cells and cells unable to support replication died. The selected cells carried large amounts of HCV RNAs detectable by Northern blot, or after metabolic radiolabeling with $^3$[H]uridine, providing formal proof that these RNAs were actively replicating in the cells. As expected for a replicative intermediate, (–) strand RNA was present in approximately 10-fold lower amounts compared to (+) strand RNA. Finally, HCV proteins could be detected by immunoprecipitation after metabolic radiolabelling with $^{35}$[S]methionine or Western blot and were confined to the cytoplasm (see also Bartenschlager and Lohmann, 2000, supra).

Although replicon titers observed in several clones generated by Lohmann et al. were several orders of magnitude higher compared to previously available cell culture-based HCV infection systems (described above, see also Blight and Gowans, Viral Hepatitis Rev., 1995, 1:143–155), the overall efficiency of clone generation upon transfection was very low. Taken together with the observation that the majority of cell clones containing replication-competent subgenomic HCV RNAs were growing much slower than the naive Huh-7 cells or the cells transformed with replication-deficient RNA, it can be concluded that the recombinant HCV replicons of Lohmann et al. are toxic to their host cells. Clearly, such cytotoxic replicons are deficient as an in vitro model of HCV propagation as they cannot attain their maximal replication titers and therefore cannot provide sufficient amounts of subgenomic viral nucleic acids required for generation of recombinant anti-viral vaccines, for studies of some of the viral processes, and for sensitive large-scale anti-viral drug screening.

In view of the above, despite the progress made in the last several years, the field is still lacking an efficient stable cell culture system for high titer propagation of recombinant HCV. Such a system is needed for (i) further studies of intracellular viral processes (e.g., analysis of HCV receptor binding, cellular infection, replication, virion assembly, and release); (ii) generation and testing of anti-viral vaccines; (iii) screening and testing of anti-viral drugs; (iv) development of targets and methods for HCV diagnostics, and (v) production of concentrated virion and protein stocks (e.g., for structural analysis of virion components leading to epitope determination for immunotherapy).

The present invention addresses these and other needs in the art by providing novel mutated recombinant HCV-derived nucleic acids and novel rapidly growing "adapted" cell clones supporting their efficient replication.

SUMMARY OF THE INVENTION

The present invention provides novel recombinant hepatitis C (HCV)-derived nucleic acids. Preferred subgenomic HCV replicons of the invention include HCVR 2 (SEQ ID NO: 2), HVCR 8 (SEQ ID NO: 3), HCVR 9 (SEQ ID NO: 4), HCVR 22 (SEQ ID NO: 5) and HCVR 24 (SEQ ID NO: 6). These replicons are derived from the parental HCV genotype 1b-based recombinant clone I377-NS3–3'UTR (SEQ ID NO: 1) and contain multiple nucleotide changes (e.g., as shown in Table I, see Example 1) which occurred following their prolonged replication in the Huh-7-derived cell clones of the present invention under stringent selection conditions. At least some of these mutations are indicative of the non-structural HCV genome regions which are responsible for high-titer viral replication and virus-induced cytotoxicity.

In a specific embodiment, the present invention is directed to plasmid clones which can be transcribed to produce self-replicating recombinant HCV RNAs of the invention.

In a separate embodiment, the instant invention includes a method for generating novel efficiently replicating recombinant HCV-derived nucleic acids containing the critical elements of the HCV replicons described above and comprising from 5' to 3' on the positive-sense nucleic acid (1) a functional 5' non-translated region (NTR) comprising an extreme 5'-terminal conserved sequence, (2) at least one open reading frame (ORF) encoding a heterologous gene operatively associated with an expression control sequence, wherein the heterologous gene and expression control sequence are oriented on the positive-strand nucleic acid molecule, (3) an ORF encoding at least a portion of an HCV polyprotein whose cleavage products form functional components of HCV virus particles and RNA replication machinery, and (4) a 3' NTR comprising an extreme 3'-terminal conserved sequence. In a specific embodiment, where the selection marker ORF is a drug resistance gene, this gene is a neomycin resistance gene (neo) operatively associated with an internal ribosome entry site (IRES).

The instant invention also includes a method for propagating the disclosed recombinant HCV-derived nucleic acids in vitro by culturing a cell line transfected or infected with an appropriate amount of HCV RNA, e.g., as produced from the plasmid clones recited above, under conditions that permit replication of the HCV RNA. In a specific embodiment, replication of the disclosed novel HCV-derived nucleic acids in susceptible cultured cells leads to the generation of potentially infectious recombinant viral particles which can be used as an attenuated anti-HCV vaccine.

Accordingly, in conjunction with the recombinant nucleic acids disclosed herein, the present invention advantageously provides cell lines, which are susceptible to HCV infection and/or transfection and support replication of such recombinant nucleic acids. In a preferred embodiment, the susceptible cell line of the invention is a human hepatoma cell line Huh-7.

The invention further provides stable "adapted" cell clones which are derived from Huh-7 cell line and are characterized by the growth properties which are similar to or indistinguishable from the naive (i.e., untransfected) Huh-7 cells (e.g., as shown in FIG. 5). According to the instant invention, these "adapted" cell clones are able to support efficient replication of subgenomic HCV RNAs. Some of the most efficiently propagating cell clones of the present invention, i.e., HCVR 2, 8, 9, 22 and 24, were deposited with the American Type Culture Collection (ATCC), 10801 University Boulevard, Manassas, Va. 20110–2209, USA on Sep. 20, 2000, and assigned Accession Nos. PTA-2489, PTA-2490, PTA-2486, PTA-2487, and PTA-2488, respectively.

The materials disclosed herein provide methods for screening (both in vitro and in vivo) for agents capable of modulating HCV infection and/or replication and/or virion assembly. Such methods include administering a candidate agent to HCV-replicating cell line(s) of the invention, and testing for an increase or decrease in a level of subgenomic HCV replication or HCV-associated protein expression compared to a level of HCV replication or HCV-associated protein expression in a control cell line transfected with replication-defective construct or in the same cell line prior to administration of the candidate agent, wherein a decrease in the level of HCV replication or HCV-associated protein expression is indicative of the inhibitory activity of the agent.

In a specific embodiment, HCV-replicating cell lines of the present invention provide a convenient system for high-throughput initial screening of potential anti-HCV therapeutics.

Further provided herein is a method for generating massive quantities of recombinant HCV replicons (which can serve as a basis for anti-HCV vaccine development) from the cell clones of the present invention, said replicons being produced either as intracellular nucleic acids or as infectious or non-infectious recombinant viral particles.

The present invention also has significant diagnostic implications. For example, the invention provides an in vitro method for detecting antibodies to HCV in a biological sample from a subject comprising contacting the sample with HCV-replicating cells, cellular fractions, isolated HCV-derived proteins, or HCV-derived viral particles prepared as described above. The contacting operation is conducted under conditions that permit binding of HCV-specific antibodies in the sample to the HCV protein(s); and detecting binding of antibodies in the sample to the HCV-derived protein(s). Detecting binding of antibodies in the sample to the HCV protein(s) is indicative of the presence of HCV infection in the subject from which the sample was derived.

In summary, the present invention provides nucleic acids encoding recombinant HCV replicons, which are capable of efficient propagation and expression of HCV-derived proteins in a cell culture system.

The invention further provides susceptible cell lines (and "adapted" rapidly growing cell clones derived from them), which support high titer replication of recombinant HCV-derived nucleic acids.

By providing cell clones supporting efficient subgenomic HCV replication, the present invention provides (i) in vitro cell culture models of HCV propagation; (ii) systems for screening candidate anti-viral compounds and evaluating drug resistance; (iii) methods for diagnosing HCV infection, and (iv) systems for production of large quantities of HCV-derived components or recombinant viral particles for antibody generation and/or vaccine development.

The present invention meets these and other objects of the invention, as set forth in greater detail in the Detailed Description and Examples, including the accompanying Drawings.

DETAILED DESCRIPTION OF THE INVENTION

Figure 1:
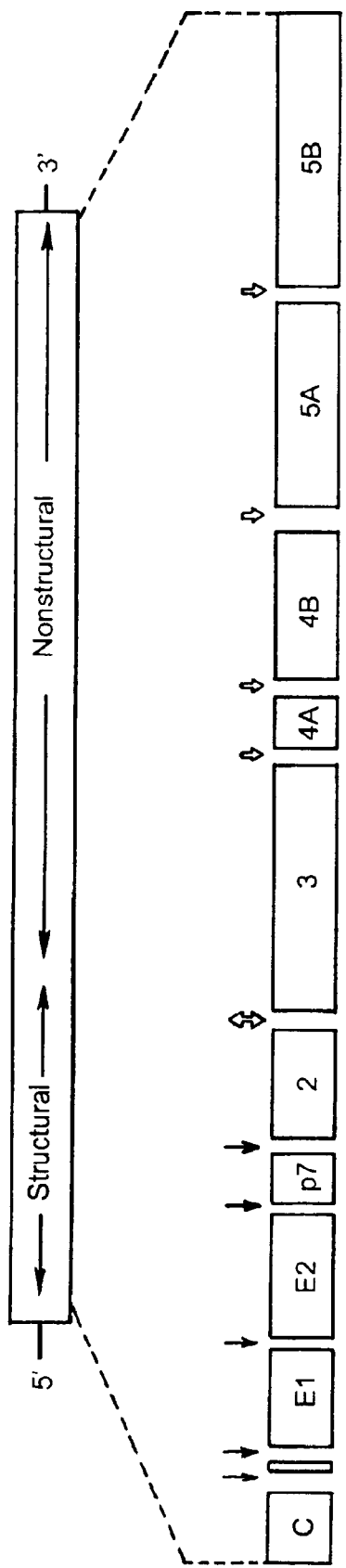
FIG. 1 (prior art) depicts HCV genome structure and polyprotein processing. At the top is a schematic representation of the viral genome with the structural and nonstructural protein coding regions, and the 5' and 3' NTRs. Boxes below the genome identify proteins generated by the proteolytic processing cascade. Different types of arrows represent different types of proteases responsible for polyprotein processing at each particular site.

All patent applications, patents, and literature references cited herein are hereby incorporated by reference in their entirety.

The present invention provides novel recombinant hepatitis C (HCV) nucleic acids containing all HCV non-translated sequences required for replication and expression, all or a portion of the HCV ORF, as well as one or more heterologous genes. In a preferred embodiment, disclosed herein are recombinant HCV-derived nucleic acids (e.g., HCVR 2 [SEQ ID NO: 2], HVCR 8 [SEQ ID NO: 3], HCVR 9 [SEQ ID NO: 4], HCVR 22 [SEQ ID NO: 5] and HCVR 24 [SEQ ID NO: 6]) which differ from the parental chimeric HCV replicon used for their generation (I377/NS3–3'UTR, SEQ ID NO: 1) in a number of positions located at various parts of the replicon genome (see, e.g., Table I). At least some of these mutant subgenomic HCV nucleic acids have a much lower cytotoxicity, as evident from their growth potential (FIG. 5) and, subsequently, have a significantly higher rate of productive transfection compared to the previously described recombinant HCV replicons. Due to these and other advantageous properties, the subgenomic HCV nucleic acids of the present invention are capable of efficient high titer replication in the susceptible cell lines of the present invention.

In conjunction with HCV-derived nucleic acids, the present invention further provides susceptible cell lines and, in particular, novel "adapted" rapidly growing cell clones derived from human hepatoma cell line Huh-7 (e.g., clones HCVR 2, 8, 9, 22 and 24), said cell lines and "adapted" clones being capable of supporting efficient replication of subgenomic recombinant HCV RNAs.

Another embodiment is a sensitive high-throughput method for screening anti-HCV therapeutics by putting them in contact with the cell clones of the present invention and determining their effect on propagation of subgenomic HCV replicons.

Further provided herein is a method for generating large quantities of recombinant HCV replicons from the cell clones of the present invention. These replicons can be generated for the purpose of providing a recombinant attenuated anti-HCV vaccine and can be produced either as intracellular nucleic acids or as infectious or non-infectious recombinant viral particles.

By providing cell clones supporting efficient subgenomic HCV replication, the present invention provides (i) in vitro cell culture models of HCV propagation; (ii) systems for screening candidate anti-viral compounds and evaluating drug resistance; (iii) methods for diagnosing HCV infection, and (iv) systems for production of large quantities of HCV-derived components or recombinant viral particles for antibody generation and/or vaccine development.

Definitions

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), in either single stranded form, or a double-stranded form. Double stranded DNA-DNA, DNA-RNA and RNA-RNA duplexes are possible. The term nucleic acid molecule, and in particular DNA or RNA molecule, refers only to the primary and secondary structure of the molecule, and does not limit it to any particular tertiary forms. In discussing the structure of particular nucleic acid molecules, sequences or regions may be described herein according to the normal convention of giving only the sequence in the 5' to 3' direction. A "recombinant DNA molecule" is a DNA molecule that has undergone a molecular biological manipulation.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. In the present invention, translation of HCV-derived (+) strand RNA initially yields a polyprotein, which is cleaved during post-translational processing to yield functional viral proteins.

The term "gene" means a DNA sequence that codes for or corresponds to a particular sequence of amino acids, which comprise all or part of one or more proteins or enzymes.

A coding sequence is "under the control" or "operatively associated with" transcriptional and translational control sequences in a cell when RNA polymerase transcribes the coding sequence into mRNA, which is then translated into the protein encoded by the coding sequence.

The terms "express" and "expression" mean allowing or causing the information in a gene or nucleic acid sequence to become manifest, for example producing a protein by activating the cellular functions involved in transcription and translation of a corresponding gene or nucleic acid sequence. A nucleic acid sequence is expressed in or by a cell to form an "expression product" such as a mRNA or a protein. The expression product itself, e.g. the resulting protein, may also be said to be "expressed" by the cell.

The term "polypeptide" refers to a polymer of amino acids and does not refer to a specific length of the product; thus, peptides, oligopeptides, and proteins are included within the definition of polypeptide. This term also does not refer to, or exclude, post-translational modifications of the polypeptide, for example, glycosylations, acetylations, phosphorylations, and the like.

As used herein, the term "conservative mutation" or "conservative nucleotide change" is used to define a nucleotide change, which occurs with high frequency within quasispecies. "Sequence-conservative variants" are those in which a change of one or more nucleotides in a given codon position results in no alteration in the amino acid encoded at that position. "Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrophobicity, size of the side chain, hydrogen bonding potential, and the like).

The term "hepatitis C virus" or "HCV" is used herein to define a viral species of which pathogenic strains cause hepatitis C, also known as non-A, non-B hepatitis.

As used herein, the term "viral RNA", which includes HCV RNA, refers to RNA from the viral genome, fragments thereof, transcripts thereof, and mutant sequences derived therefrom.

As used herein, a "(+) stranded genome" or a "positive-stranded genome" of a virus is one in which the genome, whether RNA or DNA, is single-stranded and encodes a viral or virus-derived polypeptide(s). Examples of positive-stranded RNA viruses include Togaviridae, Coronaviridae, Retroviridae, Picornaviridae, and Caliciviridae. Included also, are the Flaviviridae, which were formerly classified as Togaviridae (see Fields and Knipe, *Fundamental Virology*, Raven Press, 1986).

As used herein, a "replicative intermediate" of an HCV genome or a "(−) stranded genome" or a "negative-stranded genome" refers to an RNA strand or fragment thereof, which is complementary to the viral genome, and which is synthesized during the course of viral replication; the replicative intermediate functions as a template for the synthesis of (+) RNA strands.

As used herein, "purified HCV virions" refers to a preparation of HCV viral or virus-like particles that have been isolated from the cellular constituents with which the virus normally associates, and from other types of viruses that may be present in the infected tissue. The techniques for isolating viruses are known to those of skill in the art, and include, for example, centrifugation and affinity chromatography.

A "construct" is a chimeric virus or nucleic acid encoding a chimeric virus, such as positive viral genomic RNA or a DNA that can be transcribed to produce viral genomic RNA.

The term "chimeric" is used herein in its usual sense: a construct or protein or virus resulting from the combination of genes from two or more different sources, in which the different parts of the chimera function together. The genes are fused, where necessary in-frame, in a single genetic construct. As used herein, the term "chimeric" refers specifically to recombinant HCV-derived nucleic acids or proteins or virions.

The term "chimeric virus genome" or "recombinant virus" or "subgenomic HCV replicon" as used herein refers to the genome of the HCV that is modified by insertion or substitution of sequences. In some instances, the virus-derived replicon which later undergoes additional changes (e.g., as a result of in vitro manipulations or in vivo selection) may be referred to as a "parent" genome or replicon. In general, according to the present invention, the recombinant virus genome will include various parts of the parent virus genome, said parts comprising without limitation genes encoding proteins involved in replication, infectivity, tropism, and life cycle.

The term "junction site" is used herein to refer to the amino acid sequence joining two different proteins of a virus-derived polyprotein that is recognized and cleaved by a protease, e.g., HCV NS3. Various HCV NS3 junction sites are known, including the NS3/NS4A, NS4A/NS4B, NS4B/NS5A, and NS5A/NS5B junction sites. Any of these can be used to substitute for an endogenous junction site of the virus used in the chimeric construct.

The term "internal ribosome entry site" or "IRES" defines a special region of some viral and cellular mRNA molecules that is capable of cap-independent binding of the ribosome to initiate translation.

As used herein, "infectious" refers to the ability of a virus to enter and replicate in a cell and to produce viral particles. Infectivity can be evaluated either by detecting virus, i.e., viral load, or by observing disease progression in an animal. Virus (viral load) can be detected by the presence of viral (+) strand RNAs and/or (−) strand replication intermediates, e.g., detected by RT-PCR or direct hybridization techniques. It can also be detected, if present in sufficient amount, by the presence of replicon-derived proteins, e.g., detected by immunoassay or biochemical techniques. In another alternative, a culture medium isolated from a cell line supporting viral replication or extracts/samples from an animal are used to infect naive cells in culture. The important aspects of the determination of viral infectivity in vivo (i.e., in infected subjects) is the development of either an acute or chronic viral infection, which, in turn, may include either overt pathology or merely replication and propagation of the virus.

The term "viral load" or "viral titer" is used herein to refer to a quantitative amount of virus in a cell culture or in an infected animal. The term "titer" can be also used to refer to a quantitative amount of virus-derived replicons produced within a susceptible cell. "Disease progression" refers to the course of disease or symptoms of an infected animal, and may include acute or chronic disease symptoms. "Pathothogenesis" is a particular indication of a disease progression, and refers to the pathogenic effects of viral infection, including morbidity and mortality. In the present invention, main pathologic effects of HCV are observed in the hepatic tissue.

An "individual" or "subject" or "animal", as used herein, refers to vertebrates, particularly members of the mammalian species and includes, but is not limited to, rodents, rabbits, shrews, and primates, the latter including humans.

As used herein, a "biological sample" refers to a sample of tissue or fluid isolated from an individual, including but not limited to, for example, plasma, serum, spinal fluid, lymph fluid, the external sections of the skin, respiratory, intestinal and genitourinary tracts, tears, saliva, milk, blood cells, tumors, organs, and also samples of in vitro cell culture constituents (including, but not limited to, conditioned medium resulting from the growth of cultured cells, putatively viral infected cells, recombinant cells, and cell components).

As used herein, the term "quasispecies" means a collection of microvariants of a predominant HCV genome sequence ("master sequence"), said microvariants being formed in a single infected animal or even in a single cell clone as a result of high mutation rate during HCV replication.

As used herein, an "in vitro cell system" or an "extracorporeal cell system" refers to cells which are replicated outside of the body, i.e., cell systems not found in nature; as such, the term includes primary cultures and cell lines. "Primary cultures", as used herein, refers to a culture of cells that is directly derived from cells or tissues from an individual, as well as cells derived by passage from these cells, but not to immortalized cells.

As used herein, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, if such cell clones are capable of supporting efficient replication of HCV-derived RNAs without a significant decrease in their growth properties, they are termed "adapted" cell clones.

The term "host cell" means any cultured cell or any cell of any organism that is susceptible to infection by or propagation of a wild-type HCV or a chimeric virus construct of the invention. Host cells can further be used for screening or other assays, as described herein. A potentially susceptible cell that has not been transfected or infected with virus-derived nucleic acids is termed a "naive" cell.

The term "transfection" means the introduction of a foreign nucleic acid into a cell. The introduced gene or sequence may also be called a "cloned" or "foreign" gene or sequence, may include regulatory or control sequences, such as start, stop, promoter, signal, secretion, or other sequences used by a cellular molecular machinery. A host cell that receives and expresses introduced DNA or RNA has been "transfected" and is a "transfectant" or a "recombinant cell". According to the present invention, if a transfection of HCV-derived nucleic acid results in its subgenomic replication and HCV-derived protein expression, the transfection is termed "productive".

The term "antibody", as used herein, includes both monoclonal and polyclonal antibodies. Additionally, single polypeptide chain antigen-binding proteins, see U.S. Pat. No. 4,946,778, are included within the term "antibody".

As used herein, "epitope" refers to an antigenic determinant of a polypeptide; an epitope can comprise 3 or more amino acids in a spatial conformation unique to the epitope. Generally an epitope consists of at least 5 such amino acids and, more usually, consists of at least 8–10 such amino acids. Methods of determining the spatial conformation of amino acids are known in the art, and include, for example, x-ray crystallography and nuclear magnetic resonance (NMR).

"Immunologically identifiable with/as" refers to the presence of epitope(s) and polypeptides(s) that are also present in the designated polypeptide(s), herein usually HCV proteins. Immunological identity may be determined by antibody binding and/or competition in binding; these techniques are known to those of average skill in the art.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

As used herein, the term "immunogenic polypeptide" refers to a polypeptide that elicits a cellular and or humoral immune response, whether alone or when linked to a carrier, in the presence or absence of an adjuvant.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

General Techniques

In accordance with the present invention there may be employed conventional molecular biology, microbiology, biochemistry, genetics and immunology techniques within the skill of the art for the production of recombinant HCV nucleic acids, HCV-replicating cell cultures, infectious viral particles, viral and recombinant proteins, antibodies, etc. Such techniques are explained fully in the literature. See, e.g., Sambrook, Fritsch and Maniatis, *Molecular Cloning: A Laboratory Manual*, Second Edition, 1989, Cold Spring Harbor Laboratory Press (herein "Sambrook et al., 1989"); *DNA Cloning: A Practical Approach*, Glover ed., Volumes I and II, 1985; *Oligonucleotide Synthesis*, Gait ed., 1984; *Nucleic Acid Hybridization*, Hames and Higgins eds., 1985; *Transcription And Translation*, Hames and Higgins eds., 1984; *Animal Cell Culture*, Freshney ed., 1986; *Immobilized Cells And Enzymes*, IRL Press, 1986; Perbal, *A Practical Guide To Molecular Cloning*, 1984; *Current Protocols in Molecular Biology*, Ausubel et al., eds., 1994, John Wiley & Sons.

Construction of Recombinant HCV Replicons

In a broad aspect, the present invention is directed to genetically engineered HCV nucleic acid clones which comprise from 5' to 3' on the positive-sense nucleic acid (1) a functional 5' non-translated region (NTR) comprising an extreme 5'-terminal conserved sequence, (2) at least one open reading frame (ORF) encoding a heterologous gene operatively associated with an expression control sequence, wherein the heterologous gene and expression control sequence are oriented on the positive-strand nucleic acid molecule, (3) an ORF encoding at least a portion of an HCV polyprotein whose cleavage products form functional components of HCV virus particles and RNA replication machinery, and (4) a 3' NTR comprising an extreme 3'-terminal conserved sequence. According to the present invention, the heterologous gene can be a drug resistance gene or a reporter gene. In a specific embodiment, where the selection marker ORF is a drug resistance gene, this gene is a neomycin resistance gene (neo) operatively associated with an internal ribosome entry site (IRES). Alternatively, the heterologous gene can be a therapeutic gene, or a gene encoding a vaccine antigen, i.e., for gene therapy or gene vaccine applications, respectively.

Figure 3:
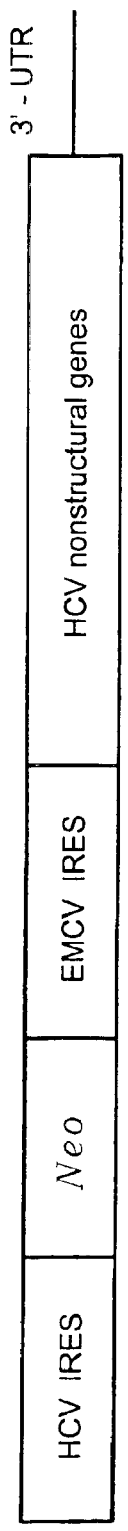
FIG. 3 is a schematic representation of the recombinant parental HCV replicon I377/NS3–3'UTR (SEQ ID NO: 1) composed of the 5'HCV-IRES, the neo gene, the EMCV-IRES, and HCV sequences from NS3 up to the authentic 3' end.
Figure 2:
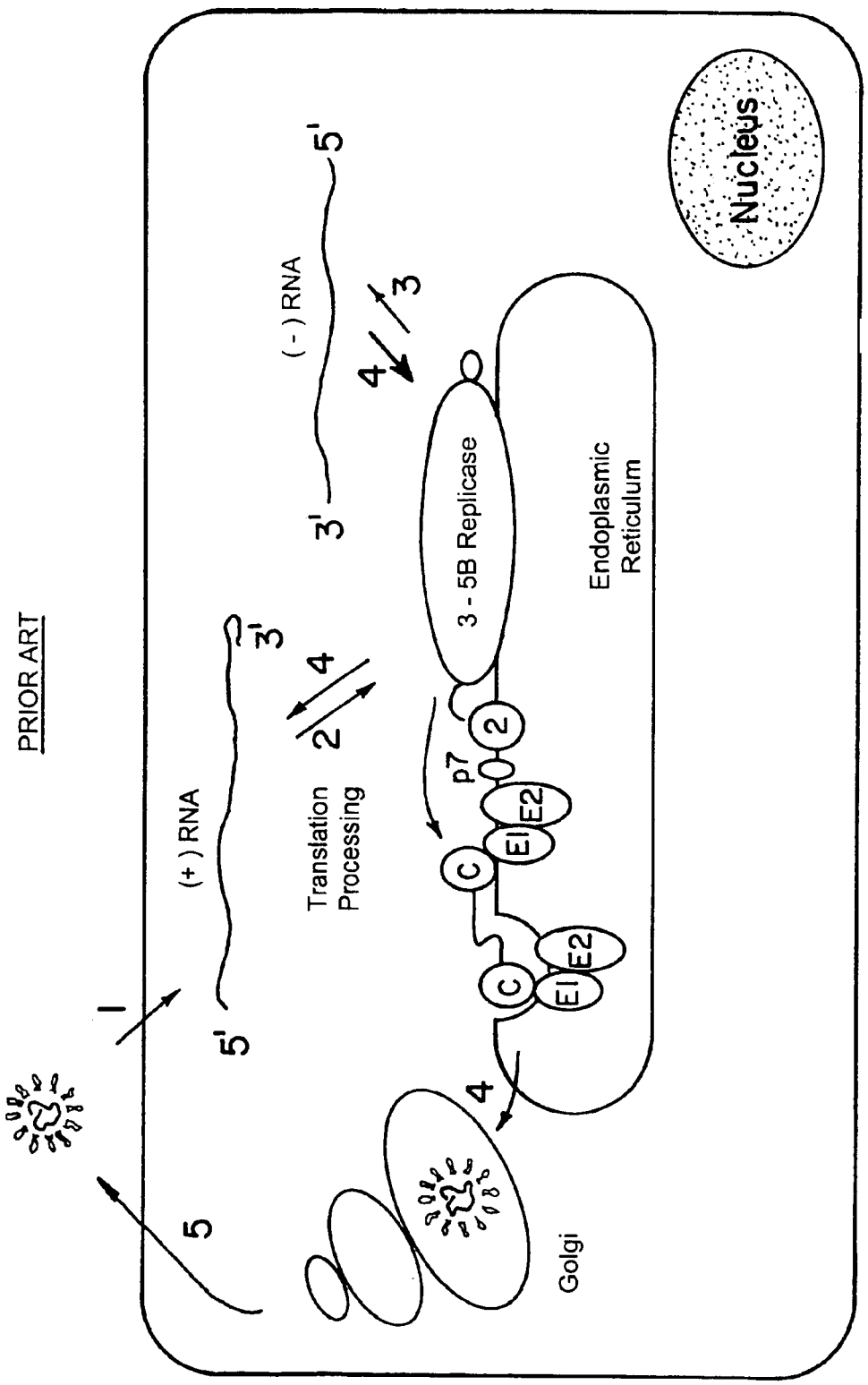
FIG. 2 (prior art) is a schematic representation of the HCV life cycle comprising the following stages: (1) penetration of the host cell and liberation of the (+) strand genomic RNA (cRNA) from the virus particle into the cytoplasm; (2) translation of the input cRNA, processing of the polyprotein and formation of a replicase complex associated with intracellular membranes; (3) utilization of the input (+) strand for synthesis of a (−) strand RNA intermediate; (4) production of new (+) strand RNA molecules which can be used for synthesis of new (−) strands, for polyprotein expression or for packaging into progeny virions; (5) release of virus from the infected cell via cellular secretion pathway resulting in formation of cell-derived viral membrane envelope.

In a preferred embodiment, the subgenomic HCV replicons are derived from a "parent" HCV genotype 1b-based chimeric replicon I377/NS3–3'UTR (SEQ ID NO: 1, see also FIG. 3). Due to their prolonged propagation under stringent selection conditions (e.g., 1 mg/ml G418, see Example 1, infra) in susceptible cell lines, the subgenomic HCV replicons of the present invention have acquired multiple mutations. Accordingly, also disclosed herein are positions of at least some of the nucleotide changes identified in these mutant HCV replicons (e.g., as shown in Table I), said nucleotide changes being indicative of the genome regions which are responsible for high-titer virus replication and for virus-induced cytotoxicity.

The actual molecular biological techniques required to generate fusion between heterologous sequences and specific fragments of HCV genome are routine. For example, a recombinant replicon can be constructed using PCR (see Lohmann et al., supra; Example 1, infra).

Naturally, as noted above, the HCV nucleic acids of the invention are selected from the group consisting of double stranded DNA, (+) strand cDNA, or (–) strand DNA, or (+) strand RNA or (–) strand RNA. Thus, where particular sequences of nucleic acids of the invention are set forth, both DNA and corresponding RNA are intended, including positive and negative strands thereof.

According to the instant invention, an HCV DNA may be inserted in a plasmid vector for transcription of the corresponding HCV RNA. Thus, the HCV DNA may comprise a promoter 5' of the 5'-NTR on (+) strand DNA, whereby transcription of template DNA from the promoter produces replication-competent RNA. The promoter can be a member selected from the group consisting of a eukaryotic promoter, yeast promoter, plant promoter, bacterial promoter, and viral promoter. The preferred promoter is phage T7 promoter (see Example 1, infra).

In a specific embodiment, the present invention is directed to a plasmid clone, pAn/HCVR1, which can be transcribed to produce self-replicating recombinant "parental" HCV RNA transcript I377/NS3–3'UTR (see FIG. 3).

Also disclosed herein are cRNA molecules transcribed from the recombinant HCV-derived DNA plasmid clones set forth above. These cRNA molecules are used for transfection into the cell lines of the present invention.

The present invention further advantageously provides DNA plasmid vectors containing inserts derived from the mutant RNA replicons disclosed herein using reverse transcription followed by PCR-amplification or other molecular biology techniques well known in the art.

Naturally, the invention also includes derivatives of all of the disclosed nucleic acids, selected from the group consisting of derivatives produced by substitution of homologous regions from other HCV isolates or genotypes; derivatives produced by mutagenesis; derivatives selected from the group consisting of infectious, adapted, live-attenuated, replication competent non-infectious, and defective variants; derivatives comprising additional heterologous gene(s) operatively associated with an expression control sequence; and derivatives consisting of a functional fragment of any of the above-mentioned derivatives. Alternatively, portions of the disclosed nucleic acids, such as the 5' NTRs, the polyprotein coding regions, the 3'-NTRs or more generally any coding or non-translated region of the HCV genome, can be substituted with a corresponding region from a different HCV genotype to generate a new chimeric clone, or by extension, clones of other isolates and genotypes. For example, an HCV-1a or -2a polyprotein coding region (or consensus polyprotein coding regions) can be substituted for the HCV-1b polyprotein coding region of the deposited clones.

By providing the engineered HCV nucleic acids of the invention, the present inventors have made it possible to dissect the HCV replication machinery and protein activity. The instant invention has also made possible the preparation of various HCV derivatives such as attenuated, expressing heterologous gene(s), replication-competent non-infectious, replication-defective infection-competent, and replication-defective non-infectious. The recombinant HCV DNA clones or RNAs of the invention can also be used in numerous methods, or to derive authentic HCV components, as set forth below.

Production of "Adapted" Cell Clones Supporting Efficient Subgenomic HCV Replication The instant invention further provides a method for propagating the disclosed recombinant HCV-derived nucleic acids in vitro comprising culturing a cell line transfected or infected with an appropriate amount of HCV RNA, e.g., as produced from the plasmid clones recited above, under conditions that permit replication of said HCV-derived RNA.

By providing novel recombinant HCV nucleic acids, in particular, nucleic acids containing mutations in the regions responsible for cytotoxicity and/or replicon titer, the present invention provides a method for generating stable cell clones supporting efficient replication of subgenomic HCV RNAs.

Accordingly, in conjunction with the recombinant nucleic acids disclosed herein, the present invention advantageously provides susceptible stable cell lines which, upon transfection or infection, can support high titer replication of the disclosed HCV-derived nucleic acids. The susceptible cell lines of the invention include without limitation human hepatoma cell lines Huh-7, HepG2, and PH5CH; T. belangeri liver cell line MBTL; human diploid fibroblast cell line VERO; secondary monkey kidney cell line CV-1; T cell lines MT-2, HPBMa10-2, and MOLT-4, and B cell line Daudi.

As disclosed herein, the HCV-replicating stable cell lines of the present invention are characterized by the growth rates which are not less than 10% of the growth rate of the corresponding naive (non-transfected) cell lines. In a preferred embodiment, these growth rates are not less than 25% of the growth rate of the corresponding naive (non-transfected) cell lines, or, even more preferably, not less than 90% of the growth rate of the corresponding naive (non-transfected) cell lines.

In a preferred embodiment, the susceptible cell line is the human hepatoma cell line Huh-7. As disclosed herein, the "adapted" cell clones derived from Huh-7 cell line support efficient replication of subgenomic HCV nucleic acids of the present invention and are characterized by the growth properties which are similar to or indistinguishable from the naive (i.e., non-transfected) Huh-7 cells (see, e.g., FIG. 5). Besides promoting the generation of novel quasispecies of recombinant replicons (e.g., containing mutations leading to lowered cytotoxicity and increased replication efficiency) these "adapted" cell clones might have acquired certain mutations in their own genomes, said mutations distinguishing them from the parental naive cells and leading to their improved ability to support replication of subgenomic HCV RNAs. Some of the most efficiently propagating cell clones of the present invention, i.e., HCVR 2, 8, 9, 22 and 24, have been deposited with the American Type Culture Collection (ATCC), 10801 University Boulevard, Manassas, Va. 20110–2209, USA on Sep. 20, 2000, and assigned Accession Nos. PTA-2489, PTA-2490, PTA-2486, PTA-2487, and PTA-2488, respectively.

The methods for detection of subgenomic HCV replicons in the cell lines of the present invention are well known in the art and include without limitation (i) Nothern blot or strand-specific reverse transcriptase-polymerase chain reaction (RT-PCR) detection of (−) strand replicative RNA intermediates; (ii) determination of an increase of (+) strand RNA using either b-DNA assay or quantitative RT-PCR, (iii) detection of expression of a heterologous reporter gene encoded by a recombinant HCV replicon (e.g., by assaying fluorescence, luminescence or enzymatic activity) and (iv) detection of HCV-derived proteins (e.g., by Westen blot or immuno-fluorescence).

The permissive cell lines that are identified using the nucleic acids of the invention are very useful, inter alia, for studying the HCV infection and propagation, isolating functional components of HCV, and for sensitive, fast diagnostic and therapeutic applications.

In a specific embodiment, the permissive cell line and the "adapted" cell clones of the present invention are used to select novel mutant recombinant HCV replicon quasispecies. By providing HCV nucleic acids comprising a selectable marker, the present invention provides a method for selecting novel mutated chimeric HCV replicons characterized by low cytotoxicity, high productive transformation efficiency, and high replicon titer attained; said method comprising (i) transformation of a susceptible cell line followed by (ii) prolonged culturing under stringent selection conditions which allow only the survival of cells supporting high titer HCV replication, and (iii) isolation of recombinant replicons from the cell clones characterized by the best growth properties. Methods for identification of the novel mutations contained within these selected replicons are well known in the art and include, for example, a sequence of steps: reverse transcription→PCR amplification-→automated sequencing→computer sequence analysis.

Production of Recombinant Virions

The invention further provides a method for producing recombinant HCV virus-like particles, comprising isolating HCV virus-like particles from the cell lines of the invention (or their culture medium) under conditions that permit subgenomic HCV replication and virus particle formation. The present invention extends to a recombinant HCV-derived virus particle comprising a replication-competent subgenomic HCV RNA, or a replication-defective HCV-derived RNA; said recombinant HCV virus particle being either infection-competent or infection-defective. In a specific embodiment the recombinant viral particles produced in the cell lines of the present invention provide an attenuated recombinant vaccine to be administered to an individual to produce an anti-viral immune response. Alternatively, isolated HCV-derived proteins expressed in the cell lines of the present invention can represent starting materials for an HCV vaccine. Preferably, a vaccine of the invention includes a pharmaceutically acceptable adjuvant. Representative but not limiting examples of adjuvants include Complete and Incomplete Freund's Adjuvant, detoxified endotoxins, mineral oils, surface active substances such as lipolecithin, pluronic polyols, polyanions, peptides, oil or hydrocarbon emulsions, immunostimulatory compounds, *Bacille Calmette-Guerin* (BCG), and the synthetic adjuvant QS-21 (McCune et al., Cancer, 1979; 43:1619).

Diagnostic and Therapeutic Applications

By providing for insertion of heterologous genes in the recombinant HCV nucleic acids, the present invention provides a method for transducing an animal susceptible to HCV infection with said heterologous genes by administering an amount of the HCV RNA to the animal either directly or in the form of infectious recombinant viral particles produced in the cell lines disclosed herein. HCV-mediated introduction of heterologous genes in susceptible animals can be useful, for example, for gene therapy or gene vaccination which is targeted to hepatic tissues.

Also provided is an in vitro cell-free assay system for HCV replication comprising HCV-derived template cRNA of the invention, e.g., as transcribed from a plasmid of the invention as set forth above, functional HCV replicase components, and an isotonic buffered medium comprising ribonucleotide triphosphate bases. These elements provide the replication machinery and raw materials (NTPs).

In a further embodiment, the invention provides a method for producing novel polyclonal antibodies to HCV-derived proteins and/or recombinant viral particles comprising administering an immunogenic amount of HCV-derived proteins isolated from the cell cultures or the in vitro cell-free system described above to an animal, and isolating generated anti-HCV antibodies. A further method for producing antibodies to HCV comprises screening a human antibody library for reactivity with HCV-derived proteins of the invention and selecting a clone from the library that expresses a reactive antibody. Alternatively, novel monoclonal anti-HCV antibodies can be produced in hybridoma cell lines using techniques well known in the art.

According to the present invention, the usefulness of newly generated antibodies can be assayed by measuring their affinity and specificity (e.g., upon their application to isolated HCV-derived antigens and/or HCV replicating cell lines of the invention and/or liver tissue sections from chronically infected animals).

The novel anti-HCV antibodies disclosed herein may be used diagnostically, e.g., to detect the presence and/or propagation of HCV in a cell culture or in an animal. Alternatively, these antibodies may be used therapeutically, e.g., in passive immunotherapy.

The present invention further advantageously provides methods for screening (both in vitro and in vivo) for agents capable of modulating HCV infection and/or replication and/or virion assembly. Such methods include administering a candidate agent to HCV infected or transfected cell line(s) of the invention, and testing for an increase or decrease in a level of subgenomic HCV replication or HCV-associated protein expression compared to a level of HCV replication or HCV-associated protein expression in a control cell line transfected with replication-defective construct or in the same cell line prior to administration of the candidate agent, wherein a decrease in the level of HCV replication (i.e., decrease in intra- or extracellular levels of recombinant HCV (+) and/or (−) RNA) or HCV-associated protein expression (e.g., decrease in intra- or extracellular levels of a reporter protein) is indicative of the inhibitory activity of the agent. Agent-mediated inhibition of virion formation can be detected microscopically (performed directly or after immunostaining); and changes in infectivity of generated HCV virus particles can be assayed by isolating them from the cell culture medium and applying to naive cells or a susceptible animal model.

In a specific embodiment, HCV-replicating cell lines of the present invention provide a convenient system for high-throughput initial screening of potential anti-HCV therapeutics. Such high-throughput screening system involves applying test compounds to the microcultures of cell clones supporting subgenomic HCV replication (growing, e.g., in 96- or 324-well microtiter plates) followed by measuring changes (e.g., using multi-plate readers or scanners) in HCV replication and/or HCV-associated protein expression and/or HCV infectivity. According to the instant invention, candidate therapeutic compounds include without limitation small molecule enzyme inhibitors (e.g., helating agents), inhibitory peptides, inhibitory (e.g., transdominant-negative) proteins, antibodies, ribozymes, and antisense nucleic acids.

A further method for screening for agents capable of modulating HCV propagation involves a cell-free system described above. This method (which can be also performed in a high-throughput format) comprises contacting the in vitro cell-free system of the invention with a candidate agent and testing for an increase or decrease in a level of HCV replication or HCV-associated protein expression compared to a level of HCV replication or HCV-associated protein expression in a control cell-based system or a control cell-free system prior to administration of the candidate agent; wherein a decrease in the level of HCV replication or HCV-associated protein expression compared to the control level is indicative of the ability of the agent to inhibit HCV propagation.

As disclosed herein, the anti-HCV therapeutic compounds identified using the initial in vitro screening methods of the present invention can be further characterized for their ability to affect subgenomic HCV propagation using secondary screens in cell cultures and/or susceptible animal models. Based on the tropism of the HCV, a preferred small animal model of the present invention is a tree shrew *Tupaia belangeri chinensis*. A preferred large animal model is a chimpanzee. Test animals will be treated with the candidate compounds that produced the strongest inhibitory effects in cell culture-based assays (control animals would not be treated, and, if available, a positive control could also be employed). A compound that protects animals from infection by the chimeric virus and/or inhibits viral propagation leading to pathogenicity, would be an attractive candidate for development of an agent for treatment/prevention of HCV infection. In addition, the animal models provide a platform for pharmacokinetic and toxicology studies.

The present invention also has significant diagnostic implications. For example, HCV-specific antibodies prepared according to the invention can be used to detect HCV presence and/or propagation in various biological samples. On the other hand, the invention provides an in vitro method for detecting antibodies to HCV in a biological sample from a subject comprising contacting said sample with HCV-replicating cells, cellular fractions, isolated HCV-derived proteins, or HCV-derived viral particles prepared as described above, under conditions that permit interaction of HCV-specific antibodies in the sample with the HCV protein (s), followed by detecting binding of the antibodies in the sample to the HCV-derived protein(s), wherein said binding is indicative of the presence of HCV infection in the subject from which the sample was derived. In the foregoing methods, the biological sample can be derived without limitation from blood, serum, plasma, blood cells, lymphocytes, or liver tissue biopsy. Techniques for isolating proteins and cellular fractions useful in the foregoing diagnostic methods are also well known in the art.

In a related aspect, the invention also provides a test kit for HCV diagnostics comprising anti-HCV antibodies, HCV virus components and/or cell lines permissive for HCV replication and expressing these components.

Taken together, the primary object of the present invention is to provide nucleic acids encoding recombinant HCV-derived replicons, which are capable of efficient propagation in a permissive cell culture system.

A related object of the invention is to provide susceptible cell lines (and "adapted" rapidly growing cell clones derived from them) which support high titer replication of recombinant HCV-derived nucleic acids.

By providing cell clones supporting efficient subgenomic HCV replication, the present invention provides (i) in vitro cell culture models of HCV propagation; (ii) systems for screening candidate anti-viral compounds and evaluating drug resistance; (iii) methods for diagnosing HCV infection, and (iv) systems for production of large quantities of HCV-derived components or recombinant viral particles for antibody generation and/or vaccine development.

EXAMPLE 1

Generation of Stable Rapidly Growing Huh-7 Hepatoma Cell Lines Which Support Efficient Replication of Subgenomic Hepatitis C Virus RNAs Materials and Methods Generation of subgenomic HCV RNAs. Parental recombinant HCV DNA construct for expression of subgenomic HCV RNAs was produced by Operon Technologies, Inc. (Alameda, Calif.) using the sequence described by Lohmann et al. (Science, 1999, supra).

Bicistronic HCV-derived DNA fragment I377/NS3–3'UTR (SEQ ID NO: 1, FIG. 3) was chemically synthesized and inserted into a modified pUC19 vector under the control of T7 promoter to produce expression plasmid pAn/HCVR1. Plasmid DNA was linearized with Sca I and used for in vitro transcription reactions with Megascript T7 In Vitro Transcription Kit (Ambion) according to manufacturer's instructions. After in vitro transcription and DNase treatment (to remove template DNA), RNA was extracted with acid phenol (Kedzierski and Porter, BioTechniques, 1991, 10:210) and used for transfections.

Cell line growth. Human hepatoma cell line Huh-7 (Nakabayashi et al., Cancer Res., 1982, 42:3858–3863) was grown in Dulbecco's Modified Eagles Medium (DMEM), supplemented with 10% Fetal Bovine Serum (FBS), Penicillin/Streptomycin, 2 mM glutamine, and non-essential amino acids, in a humidified atmosphere containing 5% $CO_2$. Cells were passaged 1–2 times per week at a split ratio of 1:4 –1:5, using trypsin/EDTA solution (0.05%/0.02%). All tissue culture reagents were from Gibco.

Cell transfection and selection of efficiently growing clones supporting high titer subgenomic HCV replication. RNA (10–30 μg) was electroporated into $0.8 \times 10^7$ cells using Gene Pulse instrument (Bio-Rad, 0,4 cm-cuvette, 450V, 960 Fa). Transfection of a construct directing the expression of firefly luciferase was used to optimize transfection efficiency. Following electroporation, cells were seeded on 10-cm culture dishes in 10 ml of growth medium. After 48 hours, G418 was added at 1 mg/ml, and the medium was changed every second day until (after 3 weeks of selection) resistant colonies were transferred to 96-well plates and passaged 1–2 times a week.

The fraction of HCV-positive cells in the total population was monitored by immunofluorescence using polyclonal antibodies raised against non-structural HCV proteins (see below) and by RT-PCR (see below; see also Lanford et al., Virology, 1994, 202:606; Shimizu et al., Proc. Natl. Acad. Sci. USA, 1992, 89:5477; Mizutani et al., J. Virol., 1996, 70:7219; Ikeda et al., Virus Res., 1998, 56:157; Fournier et al., J. Gen. Virol., 1998, 79:2376).

Stable cell clones were expanded and culture conditions were optimized to promote rapid cell growth and HCV RNA replication. Growth rates of the clones were monitored by sulphorhodamine B staining for total cellular protein. The clones which (i) had the growth properties better or indistinguishable from the naive Huh-7 cells (see, e.g., FIG. 5) and (ii) supported efficient subgenomic HCV RNA replication (as determined by quantitative RT-PCR) were chosen for further analysis.

RT-PCR assays. Total RNA was prepared from transfected cells, and serial dilutions were used for RT-PCR amplification of (i) NS5B region between nt 7435 and 7750 using primers GCCCTAGATTGTCAGATCTACG and ATAAATCCAACTGGGACGCAGC (SEQ ID NOS: 7 and 8, respectively), (ii) NS5B region between nt 7360 and 7800 using primers CCTTGTGGGCAAGGATGATCC and GACAGGCTGTGATATATGTCTCC (SEQ ID NOS: 9 and 10, respectively), and (iii) neo region between nt 650 and 1110 using primers GTTCTTTTTGTCAAGACCGACC and CCACCATGATATTCGGCAAGC (SEQ ID NOS: 11 and 12, respectively). As a control, RT-PCR was performed without template DNA or using total RNA isolated from naive Huh-7 cells.

Antibodies. Rabbit polyclonal antisera specific for HCV NS3 or NS5A (Lohmann et al., Science 1999, 285:110–113) were obtained from Ralf Bartenschlager (Institute for Virology, Johannes-Gutenberg University, Mainz, Germany). A mouse monoclonal antibody to HCV NS4B was from Virogen, Inc. (Watertown, Mass.).

In situ detection of HCV antigens using immunofluorescence. Monolayer cultures on glass coverslips were fixed with methanol-acetone mixture (1:1) for 2 min, and dried for 10 min at room temperature. Alternatively, cells were fixed directly in 6-well plates (Costar). Dried cell monolayers were blocked with 2% bovine serum albumin (BSA) in phosphate-buffered saline (PBS) for 10 min at room temperature. Double staining of cells was achieved by using rabbit anti-HCV primary antibody followed by the addition of 2 mg/ml of 4',6-diamidino-2-phenylindole (DAPI, Sigma) to stain the cellular DNA, and then secondary antibody (goat anti-rabbit IgG polyclonal antibody conjugated with rhodamine; Sigma). All primary and secondary antibodies were diluted 1:100 in blocking solution. After mounting, the samples were viewed with an Olympus BX60 microscope with a x20 or x40 objective and specific filter blocks. Images were acquired using a charge-coupled device camera (Olympus, model FKH025144) and processed using Adobe Photoshop and Canvas software.

Detection of HCV antigens by immunoblotting. Monolayer cultures of cells growing on 6-well plates were lyzed and subjected to electrophoresis in 12% or 4–20% gradient SDS-polyacrylamide gels (Laemmli, Nature, 1970, 227:680–685). After electrotransfer of proteins to a nitrocellulose filter, HCV antigens were detected using rabbit anti-HCV antibodies and Enhanced Chemiluminescence (ECL) detection kit (Amersham).

Analysis of subgenomic HCV replicons isolated from rapidly growing Huh-7 cell clones. Total RNA was isolated from HCVR 2 (SEQ ID NO: 2), HVCR 8 (SEQ ID NO: 3), HCVR 9 (SEQ ID NO: 4), HCVR 22 (SEQ ID NO: 5) and HCVR 24 (SEQ ID NO: 6) rapidly growing Huh-7 cell clones carrying replicating subgenomic HCV constructs. The whole replicon RNA was reverse-transcribed using oligonucleotide primers CTCGTATGTTGTGTGGAA and GTCGCTCTCGAGGCACATA (SEQ ID NOS: 13 and 14, respectively) designed and synthesized by Operon Technologies (Alameda, Calif.) and PCR-amplified in overlapping 0.7–1.2 kb-fragments. Total PCR products were sequenced rather then individual cDNA clones, in order to identify predominant mutations. Typically, every region was sequenced in both directions, using at least two PCR products and several primers for each direction. Sequencing was performed on a contract basis at the Children's Hospital of Philadelphia (Philadelphia, Pa.). The resulting sequences were analyzed using Sequencher™ 3.1 sequence alignment software.

Results and Discussion

Despite the availability of cloned infectious genomes, molecular studies of HCV replication and the development of antiviral drugs have been hampered by the low efficiencies of currently available cell culture systems (see overview in the Background Section).

To overcome these limitations, an efficient cell culture system was established that is based on the transfection of recombinant HCV-derived RNAs. Using chemical DNA synthesis, pAn/HCVR1 DNA plasmid was constructed, said plasmid encoding a selectable bicistronic replicon (I377/NS3–3'UTR; SEQ ID NO: 1) containing HCV 5' NTR (HCV IRES), the neomycin phosphotransferase (neo) gene, the IRES of the encephalomyocarditis virus which directs translation of HCV sequences from NS3 up to NS5B, and HCV 3' NTR (see Materials and Methods and FIG. 3).

A 5'-flanking T7 RNA polymerase promoter and an engineered restriction site at the 3' end of pAn/HCVR1 allowed for in vitro production of run-off RNA transcripts corresponding to a selectable bicistronic replicon. These in vitro transcripts (termed "parental" replicons) were transfected into Huh-7 human hepatoma cells. Particular care was taken to remove template DNA, which might otherwise integrate into transfected cells and confer G418 resistance independent of HCV replication (see Materials and Methods). The efficiency of transfection was optimized using luciferase mRNA.

In two independent transfection experiments, after 3 weeks of G418 selection (at 1 mg/ml), a total of 33 drug-resistant clones were obtained. These clones were transferred to 96-well plates and passaged 1–2 times a week. Seven cell clones were successfully expanded and were selected for further study.

Figure 4:
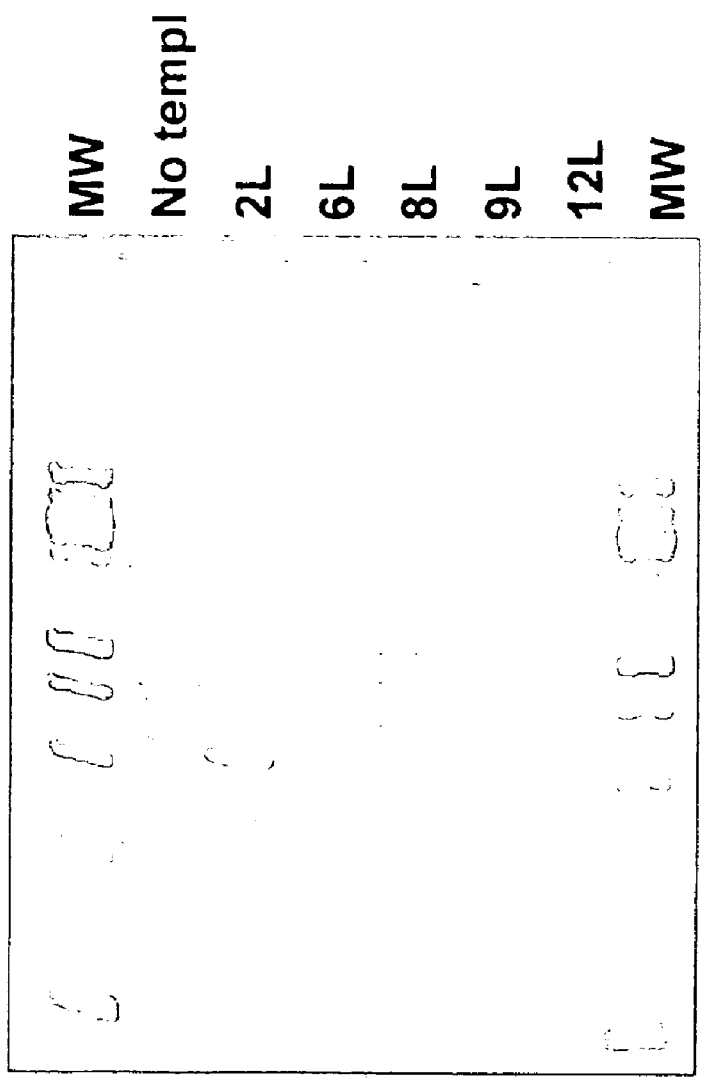
FIG. 4 depicts detection of (+) strand HCV RNA in subpassaged Huh-7 cell clones by RT-PCR using primers flanking the region corresponding to NS5B nt 7435–7750. Shown is 2% agarose gel electrophoresis analysis of RT-PCR fragments obtained by amplifying total RNA isolated from G418-resistant Huh-7 cell clones HCVR 2, 6, 8, 9 and 12 (lanes 2–6). As a negative control, PCR was performed without a DNA template (lane 1). Lane MW shows position of molecular size markers.

At five weeks posttransfection clones were analyzed by RT-PCR for the presence of HCV RNA (NS5B region was amplified, see Materials and Methods). Clones HCVR 2, 8, 9, 22 and 24 produced PCR fragments of the expected size (FIG. 4). These results were confirmed by repeating RT-PCR with three other primer pairs: two corresponding to NS5B, and one to neo gene.

Although the positive RT-PCR data and the presence of G418 resistance 5–7 weeks posttransfection are strong indications of subgenomic HCV replication, there is still a possibility that both of these effects are due to traces of the input replicon RNA. To rule out this possibility, selected Huh-7 clones which produced positive results by RT-PCR were assayed for the expression of HCV-derived NS proteins. Thus, selected clones HCVR 2, 8, 9, 22 and 24 were analyzed by immunoflurescence microscopy using anti-NS3, NS4, and NS5A antibodies (see Materials and Methods). All three viral proteins were detected in all five cell clones. Similarly to wild-type HCV which replicates in the cytoplasm, the antigens derived from the recombinant replicons of the present invention also localized to the cytoplasm. NS5A protein was expressed in a substantial fraction of cells (at least 30%) in clones HCVR 2 and HCVR 8, but not in naive Huh-7 cells. Similar pattern was observed for NS3, NS4 and NS5A proteins in all five selected cell clones.

The presence of HCV replicon-derived antigens in clones HCVR 2, 8 and 9 was also analyzed by Western blotting, and both NS5A and NS3 proteins were detected. Interestingly, when the immunofluorescence detection of NS5A was repeated at 6, 7, 8, 9, and 10 weeks posttransfection, it was found that the fraction of positive cells gradually increased with time, and at 10 weeks posttransfection over 90% of cells (in clones HCVR 8, 9, 22, 24) became HCV-positive.

Figure 5:
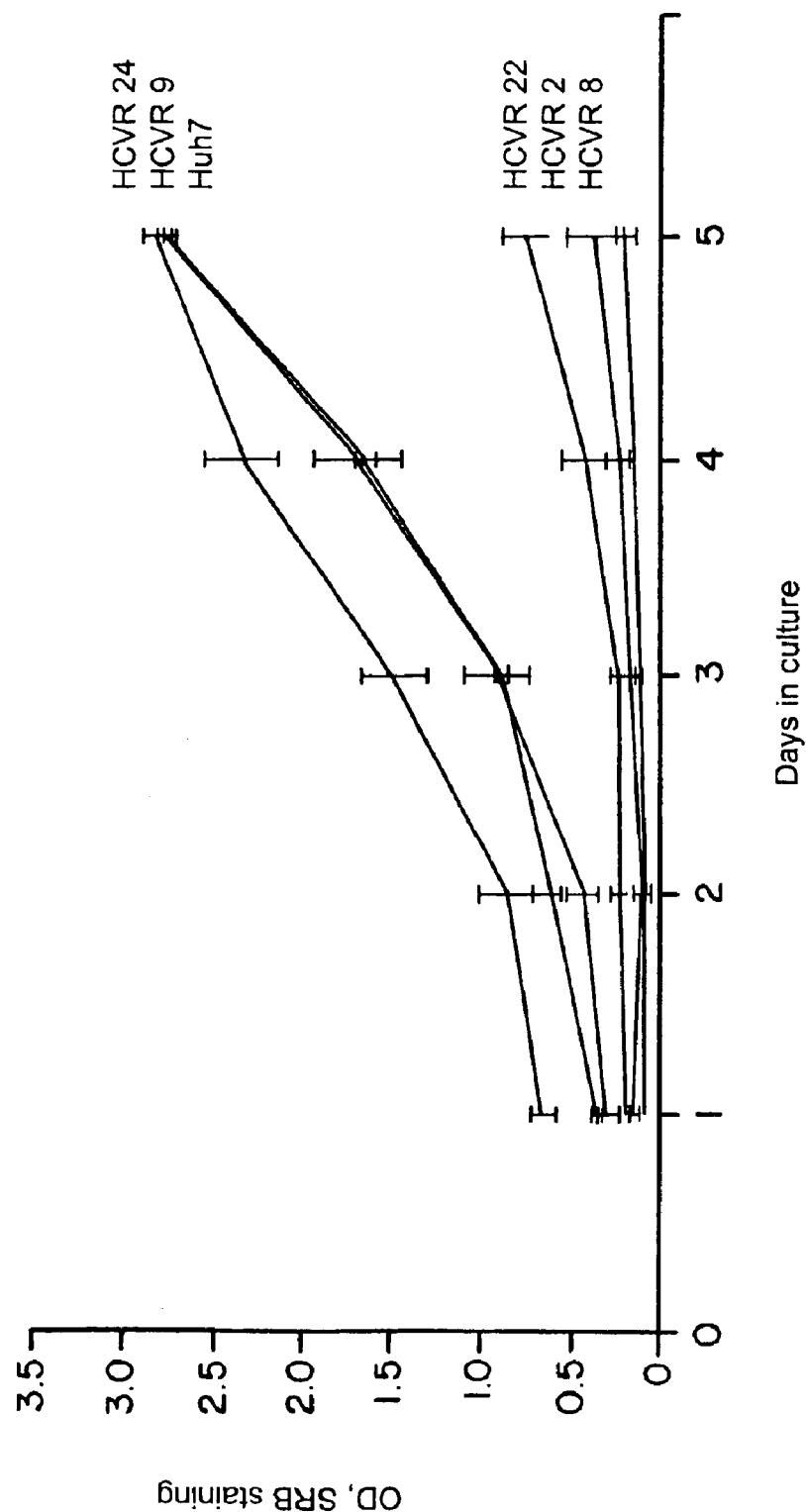
FIG. 5 is a graphic representation of relative growth rates of Huh-7-derived "adapted" cell clones supporting efficient subgenomic HCV replication. Growth rates (shown as a function of optical density after sulphorhodamine staining for total cellular proteins) of clones HCVR 2, 8, 9, 22 and 24 are compared to the growth rate of naive non-transfected Huh-7 cells (black line) at 9 weeks post-transfection.

Importantly, dramatic changes in cell growth potential were observed over time in several isolated cell clones, which were efficiently replicating subgenomic HCV. Initially (similarly to observations of Lohmann et al., Science, 1999, supra), all HCV-replicating cell lines were growing much slower as compared to the parental naive cell line, Huh-7 (i.e., growth rate of the cell lines was not more than 1% of the growth rate of naive Huh-7 cells). At certain points in time, however, (starting 6 weeks posttransfection) the growth of some of the clones began to accelerate (10-fold or more), ultimately reaching the growth rates of parental Huh-7 cells. As shown in FIG. 5, clones HCVR 9 and 24 grew at the same rate as the parental (non-transfected) Huh-7 cells. Similarly, clones HCVR 2, 8 and 22 grew only 4-fold slower than non-transfected Huh-7 cells. This is in contrast to the growth rates of cells initially prepared by reproducing experiments of Lohmann et al., which had a reduction of growth rate of at least 99% as compared to the naive cell line. Such increase in growth rates of selected clones was not previously reported and coincided with the emergence of detectable HCV-derived antigens and HCV RNA, suggesting that the observed changes were not associated with the loss of HCV replication.

In the studies of recombinant HCV replicons propagating in Huh-7 cells, Lohmann et al. did not observe any time-dependent increase in the efficiency of productive transfection and have not obtained host cell clones with normal growth properties. On the basis of these studies Lohmann et al. have hypothesized that HCV RNA replication and/or the expression of HCV NS proteins is always disadvantageous to cells. Moreover, Lohmann at eL failed to find any mutations in the 10 replicons that they have sequenced and concluded that formation of an "adapted" replicon would be rare and that the inefficiency of their system is more likely due to particular host cell conditions or factors present in only a few cells.

In contrast, the data reported here support a hypothesis that at least some of the selected replicons are "attenuated", i.e., contain mutations that are responsible for their lowered cytotoxicity and high frequency of productive transfection. To identify these mutations, replicon RNAs isolated from all five selected cell clones (HCVR 2, 8, 9, 22 and 24) were amplified using RT-PCR and sequenced. The obtained sequences (SEQ ID NOS: 2-6) were analyzed for the presence of mutations by comparing them to the sequence of the parental I377/NS3–3'UTR clone (SEQ ID NO: 1). As shown in Table I, mutations are located in various parts of the replicon genome. Further analysis of these mutations may provide important information about the evolution of the virus and the viral genes responsible for replication efficiency and cytotoxicity.

TABLE I

Mutations in Huh-7 replicon clones

| Clone # | position | change (nt) | change (aa code) | change aa | Gene |
|---|---|---|---|---|---|
| HCVR2 | 1234 | C to A | | | EMCV IRES |
| HCVR2 | 2527 | A to G | ATG to GTG | M to V | NS3 |
| HCVR2 | 5288 | G to T | CGT to CTT | R to L | NS5A |
| HCVR8 | 2330 | A to G | GAA to GGA | E to G | NS3 |
| HCVR8 | after 4847 | AAA insertion | | added K | NS5A |
| HCVR8 | 5366 | C to T | GCA to GTA | A to V | NS5A |
| HCVR9 | 1236 | | | | EMCV IRES |
| HCVR9 | 1905 | A to G | CAA to CAG | Silent | NS3 |
| HCVR9 | 3797 | A to G | AAG to AGG | K to R | NS4A |
| HCVR9 | 4364 | T to C | GTT to GCT | V to A | NS4B |
| HCVR9 | 4848 | C to A | AAC to AAA | N to K | NS5A |
| HCVR22 | 2330 | A to G | GAA to GGA | E to G | NS3 |
| HCVR22 | 3935 | A to G | CAA to CGA | Q to R | NS4B |
| HCVR22 | 5320 | G to A | GCC to ACC | A to T | NS5A |
| HCVR24 | 1760 | C to T | | | EMCV IRES |
| HCVR24 | 3016 | G to T | GAC to TAC | D to Y | NS3 |
| HCVR24 | 5336 | G to T | AGC to ATC | S to I | NS5A |

In summary, in contrast to all previous reports, using prolonged selection in the presence of G418, the present inventors have generated HCV-replicating "adapted" cell clones, which grow at the rate, which is similar to or indistinguishable from the non-transfected parental Huh-7 cell line. These cell clones support efficient propagation of recombinant HCV replicon mutants at least some of which have unusually low cytotoxicity leading to high replication titers and high cell growth rate.

Cell clones HCVR 2, 8, 9, 22 and 24, were deposited with the American Type Culture Collection (ATCC), 10801 University Boulevard, Manassas, Va. 20110–2209, USA on Sep. 20, 2000, and assigned Accession Nos. as set forth below:

ATCC Deposits

| HCV cell clone | Accession No. |
|---|---|
| HCVR 2 | PTA-2489 |
| HCVR 8 | PTA-2490 |
| HCVR 9 | PTA-2486 |
| HCVR 22 | PTA-2487 |
| HCVR 24 | PTA-2488 |

EXAMPLE 2

Screening Assays for Anti-HCV Therapeutics Using HCV-Replicating Cell Clones of the Present Invention In the identified efficiently growing "adapted" Huh-7 cell clones containing replicating recombinant HCV genomes, conditions are optimized for cell growth and HCV RNA replication. The timing of exposure to test compounds is determined based on the kinetics of HCV RNA accumulation and/or decline in the absence of the selective agent, and the effects of various known inhibitors of RNA synthesis. A cell-based assay for HCV genome replication is developed based on all these data. In this assay, candidate compounds are tested for inhibition of HCV RNA replication that is selective with respect to inhibition of cell growth. In particular, shifting of growth rate curves to a lower growth rate in the presence of a test compound indicates that the compound is a potential lead for developing an anti-HCV therapeutic.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All values given in the specification are approximate, and are provided for illustration and not by way of limitation.

What is claimed is:

1. An isolated nucleic acid molecule encoding a replication competent recombinant Hepatitis C Virus (HCV) genome having a nucleic acid sequence of HCVR 9 (SEQ ID NO: 4).

2. The isolated nucleic acid molecule according to claim 1, which nucleic acid molecule is double stranded DNA.

3. The isolated nucleic acid molecule according to claim 1, which nucleic acid molecule is single stranded DNA.

4. The isolated nucleic acid molecule according to claim 1, which nucleic acid molecule is double stranded RNA.

5. The isolated nucleic acid molecule according to claim 1, which nucleic acid molecule is single stranded RNA.

6. An isolated human hepatoma Huh-7 cell line transfected with the isolated nucleic acid molecule according to claim 1, wherein said cell line is capable of supporting efficient replication of said isolated nucleic acid.

7. The cell line of claim 6 designated HCVR 9 and having ATCC Accession No. PTA-2486.

8. The isolated nucleic acid molecule of claim 1, which is produced according to the following steps:

(a) transfecting the corresponding RNA into human hepatoma cell line Huh-7, followed by (b) culturing for about three weeks in the presence of about 1 mg/ml G418, followed by (c) transferring of resistant colonies and passaging about 1–2 times a week for at least about two more weeks, followed by (d) isolating recombinant replicons from the cell clones characterized by a growth rate which is not more than about 10-fold lower than the growth rate of the Huh-7 cell line prior to transfection.

* * * * *

UNITED STATES PATENT AND TRADEMARK OFFICE
CERTIFICATE OF CORRECTION

PATENT NO. : 6,930,095 B2
DATED : August 15, 2005
INVENTOR(S) : Vadim Bichko et al.

It is certified that error appears in the above-identified patent and that said Letters Patent is hereby corrected as shown below:

<u>Title page,</u>
Item [75], Inventors, insert -- Victor Shifrin, Newton MA (US) and Svetlana Bergelson, Newton, MA (US) --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

PATENT NO.   : 6,930,095 B2
DATED        : August 16, 2005
INVENTOR(S)  : Vadim Bichko et al.

It is certified that error appears in the above-identified patent and that said Letters Patent is hereby corrected as shown below:

<u>Title page,</u>
Item [75], Inventors, insert -- Victor Shifrin, Newton MA (US) and Svetlana Bergelson, Newton, MA (US) --.

This certificate supersedes Certificate of Correction issued April 4, 2006.

Signed and Sealed this

Eleventh Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,930,095 B2  
DATED : August 16, 2005  
INVENTOR(S) : Vadim Bichko et al.

Page 1 of 1

It is certified that error appears in the above-identified patent and that said Letters Patent is hereby corrected as shown below:

<u>Title page,</u>  
Item [75], Inventors, insert -- Victor Shifrin, Newton MA (US) and Svetlana Bergelson, Newton, MA (US) --.

This certificate supersedes Certificate of Correction issued April 4, 2006.

Signed and Sealed this

Twenty-fifth Day of April, 2006

JON W. DUDAS  
*Director of the United States Patent and Trademark Office*

SEQUENCE LISTING

<160> NUMBER OF SEQ ID NOS: 14

<210> SEQ ID NO 1
<211> LENGTH: 7992
<212> TYPE: DNA
<213> ORGANISM: Artificial Sequence
<220> FEATURE:
<223> OTHER INFORMATION: HCV replicon I377/NS3-3'UTR

<400> SEQUENCE: 1

```
gccagccccc gattgggggc gacactccac catagatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc ccccccctaa cgttactggc    1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt ccctctcgc caaaggaatg caaggtctgt tgaatgtcgt gaaggaagca    1440
gttcctctgg aagcttcttg aagacaaaca acgtctgtag cgacccttttg caggcagcgg    1500
```

```
aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tccttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga atccccttt tatggcaaag ccatccccat cgagaccatc     2880
aaggggggga ggcacctcat tttctgccat tccaagaaga atgtgatgac gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240 gaacggcct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccgaaaagcc ggccatcatt cccgacaggg aagtccttta ccgggagttc    3840
gatgagatgg aagagtgcgc ctcacacctc ccttacatcg aacagggaat gcagctcgcc    3900
```

-continued

```
gaacaattca aacagaaggc aatcgggttg ctgcaaacag ccaccaagca agcggaggct   3960
gctgctcccg tggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgccctcc accgaggacc tggttaacct actccctgct   4380
atcctctccc ctggcgccct agtcgtcggg gtcgtgtgcg cagcgatact gcgtcggcac   4440
gtgggcccag ggagggggc tgtgcagtgg atgaaccggc tgatagcgtt cgcttcgcgg    4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
caaaccacct gccatgtgg agcacagatc accggacatg tgaaaaacgg ttccatgagg    4860
atcgtggggc ctaggacctg tagtaacacg tggcatggaa cattccccat taacgcgtac   4920
accacgggcc cctgcacgcc ctccccggcg ccaaattatt ctaggcgct gtggcgggtg    4980 gctgctgagg agtacgtgga ggttacgcgg gtgggggatt tccactacgt gacgggcatg   5040
accactgaca acgtaaagtg cccgtgtcag gttccggccc ccgaattctt cacagaagtg   5100 gatgggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgacccct cccacattac ggcggagacg   5280
gctaagcgta ggctggccag gggatctccc ccctccttgg ccagctcatc agctagccag   5340
ctgtctgcgc cttccttgaa ggcaacatgc actacccgtc atgactcccc ggacgctgac   5400
ctcatcgagg ccaacctcct gtggcggcag gagatgggcg ggaacatcac ccgcgtggag   5460
tcagaaaata aggtagtaat tttggactct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggaa ggacccggac   5640
tacgtccctc cagtggtaca cggggtgtcca ttgccgcctg ccaaggcccc tccgatacca   5700
cctccacgga ggaagaggac ggttgtcctg tcagaatcta ccgtgtcttc tgccttggcg   5760
gagctcgcca caaagacctt cggcagctcc gaatcgtcgg ccgtcgacag cggcacggca   5820
acggcctctc ctgaccagcc ctccgacgac ggcgacgcgg gatccgacgt tgagtcgtac   5880
tcctccatgc ccccccttga gggggagccg gggatcccg atctcagcga cgggtcttgg    5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tgggggcaaag   6300
```

| | |
|---|---:|
| gacgtccgga acctatccag caaggccgtt aaccacatcc gctccgtgtg aaggacttg | 6360 |
| ctggaagaca ctgagacacc aattgacacc accatcatgc aaaaaatga ggttttctgc | 6420 |
| gtccaaccag agaagggggg ccgcaagcca gctcgcctta tcgtattccc agatttgggg | 6480 |
| gttcgtgtgt gcgagaaaat ggccctttac gatgtggtct ccaccctccc tcaggccgtg | 6540 |
| atgggctctt catacggatt ccaatactct cctggacagc gggtcgagtt cctggtgaat | 6600 |
| gcctggaaag cgaagaaatg ccctatgggc ttcgcatatg acacccgctg ttttgactca | 6660 |
| acggtcactg agaatgacat ccgtgttgag gagtcaatct accaatgttg tgacttggcc | 6720 |
| cccgaagcca gacaggccat aagtcgctc acagagcggc tttacatcgg ggcccctg | 6780 |
| actaattcta aagggcagaa ctgcggctat cgccggtgcc gcgcgagcgg tgtactgacg | 6840 |
| accagctgcg gtaatacct cacatgttac ttgaaggccg ctgcggcctg tcgagctgcg | 6900 |
| aagctccagg actgcacgat gctcgtatgc ggagacgacc ttgtcgttat ctgtgaaagc | 6960 |
| gcggggaccc aagaggacga ggcgagccta cgggccttca cggaggctat gactagatac | 7020 |
| tctgccccc ctggggaccc gcccaaacca gaatacgact tggagttgat aacatcatgc | 7080 |
| tcctccaatg tgtcagtcgc gcacgatgca tctggcaaaa gggtgtacta tctcacccgt | 7140 |
| gaccccacca ccccccttgc gcgggctgcg tgggagacag ctagacacac tccagtcaat | 7200 |
| tcctggctag caacatcat catgtatgcg cccaccttgt gggcaaggat gatcctgatg | 7260 |
| actcatttct tctccatcct tctagctcag gaacaacttg aaaaagccct agattgtcag | 7320 |
| atctacgggg cctgttactc cattgagcca cttgacctac ctcagatcat tcaacgactc | 7380 |
| catggcctta gcgcattttc actccatagt tactctccag gtgagatcaa tagggtggct | 7440 |
| tcatgcctca ggaaacttgg ggtaccgccc ttgcgagtct ggagacatcg ggccagaagt | 7500 |
| gtccgcgcta ggctactgtc ccagggggg agggctgcca cttgtggcaa gtacctcttc | 7560 |
| aactgggcag taaggaccaa gctcaaactc actccaatcc cggctgcgtc ccagttggat | 7620 |
| ttatccagct ggttcgttgc tggttacagc gggggagaca tatatcacag cctgtctcgt | 7680 |
| gcccgacccc gctggttcat gtggtgccta ctcctacttt ctgtaggggt aggcatctat | 7740 |
| ctactcccca accgatgaac ggggagctaa acactccagg ccaataggcc atcctgtttt | 7800 |
| tttcccttt tttttttctt tttttttttt tttttttttt tttttttttt ttctcctttt | 7860 |
| ttttcctct tttttttcctt ttctttcctt tggtggctcc atcttagccc tagtcacggc | 7920 |
| tagctgtgaa aggtccgtga gccgcttgac tgcagagagt gctgatactg gcctctctgc | 7980 |
| agatcaagta ct | 7992 |

<210> SEQ ID NO 2
<211> LENGTH: 7992
<212> TYPE: DNA
<213> ORGANISM: Artificial Sequence
<220> FEATURE:
<223> OTHER INFORMATION: HCV Replicon RNA from cell line HCVR2

<400> SEQUENCE: 2

| | |
|---|---:|
| gccagccccc gattggggc gacactccac catagatcac tccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tccttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |

```
ctcaaagaaa aaccaaaggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg    540
acctgtccgg tgccctgaat gaactgcagg acgaggcagc cgcggctatcg tggctggcca    600 cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacgcg aggatctcgt cgtgacccat ggcgatgcct    960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctacctccc ccccccctaa cgttactggc    1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttg caggcagcgg    1500 aaccccccac ctggcgacag gtgcctctgc ggccaaaagc cacgtgtata agatacacct    1560
gcaaaggcgg cacaaccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg cccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatgtgt ctaaggcaca tggtatcgac cctaacatca gaaccggggt aaggaccatc    2580
accacgggtg ccccccatca gtactccacc tatggcaagt tccttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
```

```
ctcgccaccg ctacgcctcc gggatcggtc accgtgccac atccaaacat cgaggaggtg   2820
gctctgtcca gcactggaga atccccttt tatggcaaag ccatcccat cgagaccatc    2880 aaggggggga ggcacctcat tttctgccat tccaagaaga aatgtgatga gctcgccgcg   2940
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg taggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360
ccagggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gccctgctg    3600 tataggctgg gagccgttca aaacgaggtt actaccacac accccataac caaatacatc   3660
atggcatgca tgtcggctga cctggaggtc gtcacgagca cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtccttta ccgggagttc   3840
gatgagatgg aagagtgcgc ctcacacctc ccttacatcg aacagggaat gcagctcgcc   3900
gaacaattca acagaaggc aatcgggttg ctgcaaacag ccaccaagca agcggaggct   3960
gctgctcccg tggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgcccctcc accgaggacc tggttaacct actccctgct   4380
atcctctccc ctggcgccct agtcgtcggg gtcgtgtgcg cagcgatact gcgtcggcac   4440
gtgggcccag ggggaggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc cctgccgcg attgccggga   4740 gtccccttct tctcatgtca acgtgggtac aagggagtct ggcggggcga cggcatcatg   4800
caaaccacct gccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctaggcgct gtggcgggtg   4980 gctgctgagg agtacgtgga ggttacgcgg gtgggggatt ccactacgt gacgggcatg   5040 accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
```

-continued

```
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagctta ggctgccag gggatctccc ccctccttgg ccagctcatc agctagccag     5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggaccccggac   5640 tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg gggatcccg atctcagcga cgggtcttgg     5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac cttttgacaga ctgcaggtcc tggacgacca ctaccgggac   6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg     6360 ctggaagaca ctgagacacc aattgacacc accatcatgg caaaaaatga ggttttctgc    6420
gtccaaccag agaaggggggg ccgcaagcca gctcgcctta tcgtattccc agatttgggg   6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggcccctg     6780 actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg   6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctggggaccc gcccaaacca gaatacgact tggagttgat aacatcatgc     7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccagggggg agggctgcca cttgtggcaa gtacctcttc    7560
```

| aactgggcag taaggaccaa gctcaaactc actccaatcc cggctgcgtc ccagttggat | 7620 |
| ttatccagct ggttcgttgc tggttacagc gggggagaca tatatcacag cctgtctcgt | 7680 |
| gcccgacccc gctggttcat gtggtgccta ctcctacttt ctgtaggggt aggcatctat | 7740 |
| ctactcccca accgatgaac ggggagctaa acactccagg ccaataggcc atcctgtttt | 7800 |
| tttcccttt tttttttctt ttttttttt ttttttttt ttttttttt ttctccttt | 7860 |
| ttttcctct tttttccctt ttctttcctt tggtggctcc atcttagccc tagtcacggc | 7920 |
| tagctgtgaa aggtccgtga gccgcttgac tgcagagagt gctgatactg gcctctctgc | 7980 |
| agatcaagta ct | 7992 |

<210> SEQ ID NO 3
<211> LENGTH: 7995
<212> TYPE: DNA
<213> ORGANISM: Artificial Sequence
<220> FEATURE:
<223> OTHER INFORMATION: HCV Replicon RNA from cell line HCVR8

<400> SEQUENCE: 3

| gccagccccc gattgggggc gacactccac catagatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc agggggcgcc cggttctttt tgtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agtttaaaca gaccacaacg | 1200 |
| gtttccctct agcgggatca attccgcccc tctccctccc ccccccctaa cgttactggc | 1260 |
| cgaagccgct tggaataagg ccggtgtgcg tttgtctata tgttattttc caccatattg | 1320 |
| ccgtcttttg gcaatgtgag ggcccggaaa cctggccctg tcttcttgac gagcattcct | 1380 |
| aggggtcttt cccctctcgc caaaggaatg caaggtctgt tgaatgtcgt gaaggaagca | 1440 |
| gttcctctgg aagcttcttg aagacaaaca acgtctgtag cgaccctttg caggcagcgg | 1500 |
| aaccccccac ctggcgacag gtgcctctgc ggccaaaagc cacgtgtata agatacacct | 1560 |
| gcaaaggcgg cacaacccca gtgccacgtt gtgagttgga tagttgtgga aagagtcaaa | 1620 |

```
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatggg aaccactatg    2340
cggtccccgg tcttcacgga caactcgtcc cctccggccg taccgcagac attccaggtg    2400
gcccatctac acgccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt ttcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga    3240 gaacggcct cggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca cgtggtcat tgtgggcagg    3780 atcatcttgt ccgaaagcc ggccatcatt cccgacaggg aagtccttta ccgggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
```

```
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct     4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggaggggc tgtgcagtgg atgaaccggc tgatagcgtt cgcttcgcgg      4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaaaaa cggttccatg    4860
aggatcgtgg ggcctaggac ctgtagtaac acgtggcatg gaacattccc cattaacgcg    4920
tacaccacgg gcccctgcac gccctccccg gcgccaaatt attctagggc gctgtggcgg    4980
gtggctgctg aggagtacgt ggaggttacg cgggtgggg atttccacta cgtgacgggc      5040
atgaccactg acaacgtaaa gtgcccgtgt caggttccgg cccccgaatt cttcacagaa    5100
gtggatgggg tgcggttgca caggtacgct ccagcgtgca aaccctcct acgggaggag     5160 gtcacattcc tggtcgggct caatcaatac ctggttgggt cacagctccc atgcgagccc    5220
gaaccggacg tagcagtgct cacttccatg ctcaccgacc cctcccacat tacggcggag    5280
acggctaagc gtaggctggc cagggatct cccccctcct tggccagctc atcagctagc      5340
cagctgtctg cgccttcctt gaaggcaata tgcactaccc gtcatgactc cccggacgct    5400
gacctcatcg aggccaacct cctgtggcgg caggagatgg gcgggaacat cacccgcgtg    5460
gagtcagaaa ataaggtagt aattttggac tctttcgagc cgctccaagc ggaggaggat    5520
gagagggaag tatccgttcc ggcggagatc ctgcggaggt ccaggaaatt ccctcgagcg    5580
atgcccatat gggcacgccc ggattacaac cctccactgt tagagtcctg gaaggacccg    5640
gactacgtcc ctccagtggt acacgggtgt ccattgccgc tgccaaggcc cctccgata     5700 ccacctccac ggaggaagag gacggttgtc ctgtcagaat ctaccgtgtc ttctgccttg    5760
gcggagctcg ccacaaagac cttcggcagc tccgaatcgt cggccgtcga cagcggcacg    5820
gcaacggcct ctcctgacca gccctccgac gacggcgacg cgggatccga cgttgagtcg    5880
tactcctcca tgccccccct tgaggggag ccggggatc ccgatctcag cgacgggtct        5940
tggtctaccg taagcgagga ggctagtgag gacgtcgtct gctgctcgat gtcctacaca    6000
tggacaggcg ccctgatcac gccatgcgct gcggaggaaa ccaagctgcc catcaatgca    6060
ctgagcaact ctttgctccg tcaccacaac ttggtctatg ctacaacatc tcgcagcgca    6120
agcctgcggc agaagaaggt caccttgac agactgcagg tcctggacga ccactaccgg    6180
gacgtgctca aggagatgaa ggcgaaggcg tccacagtta aggctaaact tctatccgtg    6240
gaggaagcct gtaagctgac gccccacat tcggccagat ctaaatttgg ctatgggca     6300 aaggacgtcc ggaacctatc cagcaaggcc gttaaccaca tccgctccgt gtggaaggac    6360
ttgctggaag acactgagac accaattgac accaccatca tggcaaaaaa tgaggttttc    6420
```

-continued

```
tgcgtccaac cagagaaggg gggccgcaag ccagctcgcc ttatcgtatt cccagatttg    6480
ggggttcgtg tgtgcgagaa aatggccctt tacgatgtgg tctccaccct ccctcaggcc    6540
gtgatgggct cttcatacgg attccaatac tctcctggac agcgggtcga gttcctggtg    6600
aatgcctgga aagcgaagaa atgccctatg ggcttcgcat atgacacccg ctgttttgac    6660
tcaacggtca ctgagaatga catccgtgtt gaggagtcaa tctaccaatg ttgtgacttg    6720
gcccccgaag ccagacaggc cataaggtcg ctcacagagc ggctttacat cgggggcccc    6780
ctgactaatt ctaaagggca gaactgcggc tatcgccggt gccgcgcgag cggtgtactg    6840
acgaccagct gcggtaatac cctcacatgt tacttgaagg ccgctgcggc ctgtcgagct    6900
gcgaagctcc aggactgcac gatgctcgta tgcggagacg accttgtcgt tatctgtgaa    6960
agcgcgggga cccaagagga cgaggcgagc ctacgggcct tcacggaggc tatgactaga    7020
tactctgccc ccctggggga cccgcccaaa ccagaatacg acttggagtt gataacatca    7080
tgctcctcca atgtgtcagt cgcgcacgat gcatctggca aaagggtgta ctatctcacc    7140
cgtgacccca ccaccccccct tgcgcgggct gcgtgggaga cagctagaca cactccagtc    7200
aattcctggc taggcaacat catcatgtat gcgcccaccc tgtgggcaag gatgatcctg    7260
atgactcatt tcttctccat ccttctagct caggaacaac ttgaaaaagc cctagattgt    7320
cagatctacg gggcctgtta ctccattgag ccacttgacc tacctcagat cattcaacga    7380
ctccatggcc ttagcgcatt tcactccat agttactctc caggtgagat caatagggtg    7440
gcttcatgcc tcaggaaact tggggtaccg cccttgcgag tctggagaca tcgggccaga    7500
agtgtccgcg ctaggctact gtcccagggg gggagggctg ccacttgtgg caagtacctc    7560
ttcaactggg cagtaaggac caagctcaaa ctcactccaa tcccggctgc gtcccagttg    7620
gatttatcca gctggttcgt tgctggttac agcggggag acatatatca cagcctgtct    7680
cgtgcccgac cccgctggtt catgtggtgc ctactcctac tttctgtagg ggtaggcatc    7740
tatctactcc ccaaccgatg aacggggagc taaacactcc aggccaatag gccatcctgt    7800
ttttttccct tttttttttt ctttttttttt ttttttttttt tttttttttt tttttctcct    7860
ttttttttcc tcttttttttc cttttctttc ctttggtggc tccatcttag ccctagtcac    7920
ggctagctgt gaaaggtccg tgagccgctt gactgcagag agtgctgata ctggcctctc    7980
tgcagatcaa gtact                                                    7995
```

<210> SEQ ID NO 4
<211> LENGTH: 7992
<212> TYPE: DNA
<213> ORGANISM: Artificial Sequence
<220> FEATURE:
<223> OTHER INFORMATION: HCV Replicon RNA from cell line HCVR9

<400> SEQUENCE: 4

```
gccagccccc gattgggggc gacactccac catagatcac tcccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
```

-continued

```
ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacgcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc    1260
cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaggaatg caaggtctgt tgaatgtcgt gaaggaagca    1440
gttcctctgg aagcttcttg aagacaaaca acgtctgtag cgacccttt caggcagcgg   1500
aaccccccac ctggcgacag gtgcctctgc ggccaaaagc cacgtgtata agatacacct   1560
gcaaaggcgg cacaaccca gtgccacgtt gtgagttgga tagttgtgga aagagtcaaa    1620
tggctctcct caagcgtatt caacaagggg ctgaaggatg cccagaaggt accccattgt   1680
atgggatctg atctggggcc tcggtgcaca tgctttacat gtgtttagtc gaggttaaaa   1740
aacgtctagg cccccgaac cacggggacg tggttttcct ttgaaaaaca cgataatacc    1800
atggcgccta ttacggccta ctcccaacag acgcgaggcc tacttggctg catcatcact   1860
agcctcacag gccgggacag gaaccaggtc gaggggagg tccaggtggt ctccaccgca    1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgcccccc ggggcgcgtt ccttgacacc atgcacctgc   2100
ggcagctcgg acctttactt ggtcacgagg catgccgatg tcattccggt gcgccggcgg   2160
ggcgacagca gggggagcct actctccccc aggcccgtcc cctacttgaa gggctcttcg   2220
ggcggtccac tgctctgccc ctcggggcac gctgtgggca tctttcgggc tgccgtgtgc   2280
acccgagggg ttgcgaaggc ggtggacttt gtacccgtcg agtctatgga aaccactatg   2340
cggtccccgg tcttcacgga caactcgtcc cctccggccg taccgcagac attccaggtg   2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacggggtg cccccatcac gtactccacc tatggcaagt ttcttgccga cggtggttgc   2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtccac atccaaacat cgaggaggtg   2820
gctctgtcca gcactggaga aatccccttt tatggcaaag ccatccccat cgagaccatc   2880
```

-continued

```
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaggcc ggccatcatt cccgacaggg aagtccttta ccgggagttc    3840
gatgagatgg aagagtgcgc ctcacacctc ccttacatcg aacagggaat gcagctcgcc    3900
gaacaattca acagaaggc aatcggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggctaacct actccctgct    4380
atcctctccc ctggcgccct agtcgtcggg gtcgtgtgcg cagcgatact gcgtcggcac    4440
gtgggcccag ggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaaggg ttccatgagg    4860
atcgtggggc ctaggacctg tagtaacacg tggcatggaa cattccccat taacgcgtac    4920
accacgggcc cctgcacgcc ctcccggcg ccaaattatt ctaggcgct gtggcgggtg    4980 gctgctgagg agtacgtgga ggttacgcgg gtgggggatt ccactacgt gacgggcatg    5040 accactgaca acgtaaagtg cccgtgtcag gttccggccc cgaattctt cacagaagtg    5100 gatggggtgc ggttgcacag gtacgctcca gcgtgcaaac ccctcctacg ggaggaggtc    5160
acattcctgg tcgggctcaa tcaataccctg gttgggtcac agctcccatg cgagcccgaa    5220
ccggacgtag cagtgctcac ttccatgctc accgaccct cccacattac ggcggagacg    5280
```

```
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaaggggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggcccctg    6780 actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctgggacccc gcccaaacca gaatacgact tggagttgat aacatcatgc    7080
tcctccaatg tgtcagtcgc gcacgatgca tctggcaaaa gggtgtacta tctcacccgt    7140
gaccccacca cccccccttgc gcgggctgcg tgggagacag ctagacacac tccagtcaat    7200
tcctggctag gcaacatcat catgtatgcg cccaccttgt gggcaaggat gatcctgatg    7260 actcattlct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggacacatcg ggccagaagt    7500
gtccgcgcta ggctactgtc ccagggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
```

-continued

| | |
|---|---|
| gcccgacccc gctggttcat gtggtgccta ctcctacttt ctgtaggggt aggcatctat | 7740 |
| ctactcccca accgatgaac ggggagctaa acactccagg ccaataggcc atcctgtttt | 7800 |
| tttcccttt ttttttttctt tttttttttt tttttttttt tttttttttt ttctccttt | 7860 |
| ttttcctct tttttttcctt ttctttcctt tggtggctcc atcttagccc tagtcacggc | 7920 |
| tagctgtgaa aggtccgtga gccgcttgac tgcagagagt gctgatactg gcctctctgc | 7980 |
| agatcaagta ct | 7992 |

<210> SEQ ID NO 5
<211> LENGTH: 7992
<212> TYPE: DNA
<213> ORGANISM: Artificial Sequence
<220> FEATURE:
<223> OTHER INFORMATION: HCV Replicon from cell line HCVR22

<400> SEQUENCE: 5

| | |
|---|---|
| gccagccccc gattgggggc gacactccac catagatcac tccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc aggggcgccc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agtttaaaca gaccacaacg | 1200 |
| gtttccctct agcgggatca attccgcccc tctccctccc ccccccctaa cgttactggc | 1260 |
| cgaagccgct tggaataagg ccggtgtgcg tttgtctata tgttattttc caccatattg | 1320 |
| ccgtcttttg gcaatgtgag ggcccggaaa cctggccctg tcttcttgac gagcattcct | 1380 |
| aggggtcttt cccctctcgc caaaggaatg caaggtctgt tgaatgtcgt gaaggaagca | 1440 |
| gttcctctgg aagcttcttg aagacaaaca acgtctgtag cgaccctttg caggcagcgg | 1500 |
| aaccccccac ctggcgacag gtgcctctgc ggccaaaagc cacgtgtata agatacacct | 1560 |
| gcaaaggcgg cacaaccccca gtgccacgtt gtgagttgga tagttgtgga aagagtcaaa | 1620 |
| tggctctcct caagcgtatt caacaagggg ctgaaggatg cccagaaggt acccccattgt | 1680 |
| atgggatctg atctggggcc tcggtgcaca tgctttacat gtgtttagtc gaggttaaaa | 1740 |

```
aacgtctagg ccccccgaat cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatggg aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacggggtg cccccatcac gtactccacc tatggcaagt ttcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatcccat cgagaccatc    2880
aagggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca cgtggtcat tgtgggcagg    3780
atcatcttgt ccgaaagcc ggccatcatt cccgacaggg aagtcctta ccgggagttc    3840
gatgagatgg aagagtgcgc ctcacacctc ccttacatcg aacagggaat gcagctcgcc    3900
gaacaattca aacagaaggc aatcgggttg ctgcgaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
```

-continued

```
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggaggggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaataccctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460 tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cggggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta gctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggcccttttac gatgtggtct ccaccctccc tcaggccgtg    6540
```

```
atgggctctt catacggatt ccaatactct cctggacagc gggtcgagtt cctggtgaat     6600
gcctggaaag cgaagaaatg ccctatgggc ttcgcatatg acacccgctg ttttgactca     6660
acggtcactg agaatgacat ccgtgttgag gagtcaatct accaatgttg tgacttggcc     6720
cccgaagcca gacaggccat aaggtcgctc acagagcggc tttacatcgg ggcccccctg     6780
actaattcta aagggcagaa ctgcggctat cgccggtgcc gcgcgagcgg tgtactgacg     6840
accagctgcg gtaataccct cacatgttac ttgaaggccc tgcgcgcctg tcgagctgcg     6900
aagctccagg actgcacgat gctcgtatgc ggagacgacc ttgtcgttat ctgtgaaagc     6960
gcggggaccc aagaggacga ggcgagccta cgggccttca cggaggctat gactagatac     7020
tctgcccccc ctgggacccc gcccaaacca gaatacgact tggagttgat aacatcatgc     7080
tcctccaatg tgtcagtcgc gcacgatgca tctggcaaaa gggtgtacta tctcacccgt     7140
gaccccacca cccccccttgc gcgggctgcg tgggagacag ctagacacac tccagtcaat     7200
tcctggctag gcaacatcat catgtatgcg cccaccttgt gggcaaggat gatcctgatg     7260
actcatttct tctccatcct tctagctcag gaacaacttg aaaaagccct agattgtcag     7320
atctacgggg cctgttactc cattgagcca cttgacctac ctcagatcat tcaacgactc     7380
catggcctta gcgcattttc actccatagt tactctccag gtgagatcaa tagggtggct     7440
tcatgcctca ggaaacttgg ggtaccgccc ttgcgagtct ggagacatcg ggccagaagt     7500
gtccgcgcta ggctactgtc ccaggggggg agggctgcca cttgtggcaa gtacctcttc     7560
aactgggcag taaggaccaa gctcaaactc actccaatcc cggctgcgtc ccagttggat     7620
ttatccagct ggttcgttgc tggttacagc gggggagaca tatatcacag cctgtctcgt     7680
gcccgacccc gctggttcat gtggtgccta ctcctacttt ctgtaggggt aggcatctat     7740
ctactcccca accgatgaac ggggagctaa acactccagg ccaataggcc atcctgtttt     7800
tttccctttt tttttttctt tttttttttt tttttttttt ttttttttt ttctcctttt     7860 tttttcctct tttttccttt tcttttcctt tggtggctcc atcttagccc tagtcacggc     7920
tagctgtgaa aggtccgtga gccgcttgac tgcagagagt gctgatactg gcctctctgc     7980
agatcaagta ct                                                         7992
```

<210> SEQ ID NO 6
<211> LENGTH: 7992
<212> TYPE: DNA
<213> ORGANISM: Artificial Sequence
<220> FEATURE:
<223> OTHER INFORMATION: HCV Replicon from cell line HCVR24

<400> SEQUENCE: 6

```
gccagccccc gattgggggc gacactccac catagatcac tccctgtga ggaactactg       60 tcttcacgca gaaagcgtct agccatggcg ttagtatgag tgtcgtgcag cctccaggac      120
ccccctcccc gggagagcca tagtggtctg cggaaccggt gagtacaccg gaattgccag      180
gacgaccggg tcctttcttg gatcaacccg ctcaatgcct ggagatttgg gcgtgccccc      240
gcgagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaaggg cgcgccatga ttgaacaaga tggattgcac gcaggttctc      420
cggccgcttg ggtggagagg ctattcggct atgactgggc acaacagaca atcggctgct      480
ctgatgccgc cgtgttccgg ctgtcagcgc agggcgcccc ggttcttttt gtcaagaccg      540
acctgtccgg tgccctgaat gaactgcagg acgaggcagc gcggctatcg tggctggcca      600
```

-continued

```
cgacgggcgt tccttgcgca gctgtgctcg acgttgtcac tgaagcggga agggactggc      660
tgctattggg cgaagtgccg gggcaggatc tcctgtcatc tcaccttgct cctgccgaga      720
aagtatccat catggctgat gcaatgcggc ggctgcatac gcttgatccg gctacctgcc      780
cattcgacca ccaagcgaaa catcgcatcg agcgagcacg tactcggatg gaagccggtc      840
ttgtcgatca ggatgatctg gacgaagagc atcaggggct cgcgccagcc gaactgttcg      900
ccaggctcaa ggcgcgcatg cccgacggcg aggatctcgt cgtgacccat ggcgatgcct      960
gcttgccgaa tatcatggtg gaaaatggcc gcttttctgg attcatcgac tgtggccggc     1020
tgggtgtggc ggaccgctat caggacatag cgttggctac ccgtgatatt gctgaagagc     1080
ttggcggcga atgggctgac cgcttcctcg tgctttacgg tatcgccgct cccgattcgc     1140
agcgcatcgc cttctatcgc cttcttgacg agttcttctg agtttaaaca gaccacaacg     1200
gtttccctct agcgggatca attccgcccc tctccctccc cccccctaa cgttactggc     1260
cgaagccgct tggaataagg ccggtgtgcg tttgtctata tgttattttc caccatattg     1320
ccgtcttttg gcaatgtgag ggcccggaaa cctggccctg tcttcttgac gagcattcct     1380
aggggtcttt cccctctcgc caaaggaatg caaggtctgt tgaatgtcgt gaaggaagca     1440
gttcctctgg aagcttcttg aagacaaaca acgtctgtag cgaccctttg caggcagcgg     1500
aacccccac ctggcgacag gtgcctctgc ggccaaaagc cacgtgtata agatacacct     1560
gcaaaggcgg cacaacccca gtgccacgtt gtgagttgga tagttgtgga aagagtcaaa     1620
tggctctcct caagcgtatt caacaagggg ctgaaggatg cccagaaggt accccattgt     1680
atgggatctg atctggggcc tcggtgcaca tgctttacat gtgtttagtc gaggttaaaa     1740
aacgtctagg cccccgaac cacggggacg tggttttcct ttgaaaaaca cgataatacc     1800
atggcgccta ttacggccta ctcccaacag acgcgaggcc tacttggctg catcatcact     1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc     1980
ggctcaaaga cccttgccgg cccaaagggc ccaatcaccc aaatgtacac caatgtggac     2040
caggacctcg tcggctggca agcgcccccc ggggcgcgtt ccttgacacc atgcacctgc     2100
ggcagctcgg acctttactt ggtcacgagg catgccgatg tcattccggt gcgccggcgg     2160
ggcgacagca gggggagcct actctccccc aggcccgtct cctacttgaa gggctcttcg     2220
ggcggtccac tgctctgccc ctcggggcac gctgtgggca tctttcgggc tgccgtgtgc     2280
acccgagggg ttgcgaaggc ggtggacttt gtacccgtca gtctatgga aaccactatg     2340
cggtccccgg tcttcacgga caactcgtcc cctccggccg taccgcagac attccaggtg     2400
gcccatctac acgcccctac tggtagcggc aagagcacta aggtgccggc tgcgtatgca     2460
gcccaagggt ataaggtgct tgtcctgaac ccgtccgtcg ccgccaccct aggtttcggg     2520
gcgtatatgt ctaaggcaca tggtatcgac cctaacatca gaaccggggt aaggaccatc     2580
accacgggtg cccccatcac gtactccacc tatggcaagt tccttgccga cggtggttgc     2640
tctgggggcg cctatgacat cataatatgt gatgagtgcc actcaactga ctcgaccact     2700
atcctgggca tcggcacagt cctggaccaa gcggagacgg ctggagcgcg actcgtcgtg     2760
ctcgccaccc tacgcctcc gggatcggtc accgtgccac atcaaacat cgaggaggtg     2820
gctctgtcca gcactggaga atccccttt tatggcaaag ccatccccat cgagaccatc     2880
aagggggga ggcacctcat tttctgccat tccaagaaga atgtgatga gctcgccgcg     2940
aagctgtccg gcctcggact caatgctgta gcatattacc ggggccttga tgtatccgtc     3000
```

```
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga    3240
gaacggccct cggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccgaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcggggtg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt taacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtggggattt ccactacgt gacgggcatg    5040 accactgaca acgtaaagtg cccgtgtcag gttccggccc cgaattctt cacagaagtg    5100 gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctgccag gggatctccc ccctccttgg ccagctcatc agctatccag    5340
ctgtctgcgc cttccttgaa ggcaacatgc actacccgtc atgactcccc ggacgctgac    5400
```

```
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaaggggg ccgcaagcca gctcgcctta tcgtattccc agatttgggg    6480
gttcgtgtgt gcgagaaaat ggcccttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggcccctg    6780 actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctgggacccc gcccaaacca gaatacgact tggagttgat aacatcatgc    7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccagggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
gcccgacccc gctggttcat gtggtgccta ctcctacttt ctgtagggt aggcatctat    7740 ctactcccca accgatgaac ggggagctaa acactccagg ccaataggcc atcctgtttt    7800
```

```
tttcccttttt tttttttcttt ttttttttttt ttttttttttt ttctccttttt       7860 ttttcctct   tttttccctt  ttctttcctt  tggtggctcc  atcttagccc  tagtcacggc  7920
tagctgtgaa  aggtccgtga  gccgcttgac  tgcagagagt  gctgatactg  gcctctctgc  7980
agatcaagta ct                                                    7992

<210> SEQ ID NO 7
<211> LENGTH: 22
<212> TYPE: DNA
<213> ORGANISM: Artificial Sequence
<220> FEATURE:
<223> OTHER INFORMATION: primer for NS5B region between nt 7435 and 7750

<400> SEQUENCE: 7
gccctagatt gtcagatcta cg                                         22

<210> SEQ ID NO 8
<211> LENGTH: 22
<212> TYPE: DNA
<213> ORGANISM: Artificial Sequence
<220> FEATURE:
<223> OTHER INFORMATION: primer for NS5B region between nt 7435 and 7750

<400> SEQUENCE: 8
ataaatccaa ctgggacgca gc                                         22

<210> SEQ ID NO 9
<211> LENGTH: 21
<212> TYPE: DNA
<213> ORGANISM: Artificial Sequence
<220> FEATURE:
<223> OTHER INFORMATION: primer for NS5B region between 7360 and 7800

<400> SEQUENCE: 9
ccttgtgggc aaggatgatc c                                          21

<210> SEQ ID NO 10
<211> LENGTH: 23
<212> TYPE: DNA
<213> ORGANISM: Artificial Sequence
<220> FEATURE:
<223> OTHER INFORMATION: primer for NS5B region between nt 7360 and 7800

<400> SEQUENCE: 10
gacaggctgt gatatatgtc tcc                                        23

<210> SEQ ID NO 11
<211> LENGTH: 22
<212> TYPE: DNA
<213> ORGANISM: Artificial Sequence
<220> FEATURE:
<223> OTHER INFORMATION: primer for neo region between nt 650 and 1110

<400> SEQUENCE: 11 gttcttttg tcaagaccga cc                                          22

<210> SEQ ID NO 12
<211> LENGTH: 21
<212> TYPE: DNA
<213> ORGANISM: Artificial Sequence
<220> FEATURE:
<223> OTHER INFORMATION: primer for neo region between nt 650 and 1110

<400> SEQUENCE: 12
ccaccatgat attcggcaag c                                          21
```

```
<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 13
ctcgtatgtt gtgtggaa                                                  18

<210> SEQ ID NO 14
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 14
gtcgctctcg aggcacata                                                 19
```